(12) United States Patent
Washburn et al.

(10) Patent No.: US 10,377,832 B2
(45) Date of Patent: Aug. 13, 2019

(54) MODIFIED GLYCOPROTEINS

(71) Applicant: Momenta Pharmaceuticals, Inc., Cambridge, MA (US)

(72) Inventors: Nathaniel Washburn, Littleton, MA (US); James Meador, III, Framingham, MA (US); Carlos J. Bosques, Arlington, MA (US); Dorota A. Bulik, Malden, MA (US); Naveen Bhatnagar, Framingham, MA (US); Julia Brown, Somerville, MA (US); Lynn Markowitz, Waltham, MA (US); Sathya Prabbhakar, Boxborough, MA (US)

(73) Assignee: Momenta Pharmaceuticals, Inc., Cambridge, MA (US)

( * ) Notice: Subject to any disclaimer, the term of this patent is extended or adjusted under 35 U.S.C. 154(b) by 43 days.

(21) Appl. No.: 15/497,057

(22) Filed: Apr. 25, 2017

(65) Prior Publication Data

US 2017/0349662 A1    Dec. 7, 2017

Related U.S. Application Data

(62) Division of application No. 14/396,420, filed as application No. PCT/US2013/037997 on Apr. 24, 2013, now Pat. No. 9,663,581.

(60) Provisional application No. 61/638,099, filed on Apr. 25, 2012.

(51) Int. Cl.
*C07K 16/00* (2006.01)
*C07K 16/28* (2006.01)

(52) U.S. Cl.
CPC .......... *C07K 16/2887* (2013.01); *C07K 16/00* (2013.01); *C07K 2317/41* (2013.01); *C07K 2317/52* (2013.01); *C07K 2317/524* (2013.01); *C07K 2317/526* (2013.01); *C07K 2317/71* (2013.01); *C07K 2317/732* (2013.01); *C07K 2317/734* (2013.01); *C07K 2319/30* (2013.01)

(58) Field of Classification Search
None
See application file for complete search history.

(56) References Cited

U.S. PATENT DOCUMENTS

| | | |
|---|---|---|
| 5,047,335 A | 9/1991 | Paulson et al. |
| 5,278,299 A | 1/1994 | Wong et al. |
| 5,510,261 A | 4/1996 | Goochee et al. |
| 5,624,821 A | 4/1997 | Winter et al. |
| 6,194,551 B1 | 2/2001 | Idusogie et al. |
| 6,676,927 B1 | 1/2004 | Ravetch |
| 8,093,359 B2 | 1/2012 | Lazar et al. |
| 8,188,231 B2 | 5/2012 | Lazar et al. |
| 9,663,581 B2 | 5/2017 | Washburn et al. |
| 2006/0088906 A1 | 4/2006 | DeFrees et al. |
| 2007/0003546 A1 | 1/2007 | Lazar et al. |
| 2007/0111281 A1 | 5/2007 | Sondermann et al. |
| 2007/0148164 A1 | 6/2007 | Farrington et al. |
| 2009/0087478 A1 | 4/2009 | Hansen et al. |
| 2009/0288178 A1 | 11/2009 | Jarvis |
| 2010/0184959 A1 | 7/2010 | Guler-Gane et al. |
| 2015/0299331 A1 | 10/2015 | Washburn et al. |

FOREIGN PATENT DOCUMENTS

| | | |
|---|---|---|
| WO | WO-99/51642 A1 | 10/1999 |
| WO | WO-2007/039818 A2 | 4/2007 |
| WO | WO-2008/057634 A2 | 5/2008 |
| WO | WO-2009/132130 A2 | 10/2009 |
| WO | WO-2011/149999 A2 | 12/2011 |
| WO | WO-2012/162160 A1 | 11/2012 |

OTHER PUBLICATIONS

Arnold, J. et al., Human serum IgM glycosylation: identification of glycoforms that can bind to mannan-binding lectin, Journal of Biological Chemistry, 280(32):29080-29087 (2005).
Bowman, K. and Bertozzi, C., Carbohydrate sulfotransferases: mediators of extracellular communication, Chemistry and Biology, 6(1):R9-R22 (1999).
Bruggemann, M. et al., Comparison of the effector functions of human immunoglobulins using a matched set of chimeric antibodies, Journal of Experimental Medicine, 166(5):1351-1361 (1987).
Cassel, D. et al., Differential expression of Fc gamma RIIA, Fc gamma RIIB and Fc gamma RIIC in hematopoietic cells: analysis of transcripts, Molecular Immunology, 30(5):451-460 (1993).
Clynes, R. et al., Fc receptors are required in passive and active immunity to melanoma, Proceedings of the National Academy of Sciences USA, 95(2):652-656 (1998).
Clynes, R. et al., Inhibitory Fc receptors modulate in vivo cytotoxicity against tumor targets, Nature Medicine, 6(4):443-446 (2000).
Dall'Acqua, W. et al., Increasing the Affinity of a Human IgG1 for the Neonatal Fc Receptor: Biological Consequences, The Journal of Immunology, 169:5171-5180 (2002).
Daëron, M., Fc receptor biology, Annual Review of Immunology, 15:203-234 (1997).
Duncan, A. et al., Localization of the binding site for the human high-affinity Fc receptor on IgG, Nature, 332(6164):563-564 (1988).
Extended European Search Report for 13781339.0, 9 pages (dated Aug. 14, 2015).
Falany, Charles N., Enzymology of human cytosolic sulfotransferases, The FASEB Journal, 11(4):206-216 (1997).
Ferrara, C. et al., Unique carbohydrate-carbohydrate interactions are required for high affinity binding between FcγRIII and antibodies lacking core fucose, Proceedings of the National Academy of Sciences, 108(31):12669-12674 (2011).
GenBank Accession No. NP_003645, CHST1 (2015).

(Continued)

*Primary Examiner* — Hong Sang
(74) *Attorney, Agent, or Firm* — Choate Hall & Stewart LLP; Brenda Herschbach Jarrell; Rolando Medina

(57) ABSTRACT

Modified glycoproteins, and methods of making and using such modified glycoproteins, are described.

15 Claims, 8 Drawing Sheets
Specification includes a Sequence Listing.

(56) References Cited

OTHER PUBLICATIONS

GenBank Accession No. NP_005760, CHST4 (2015).
GenBank Accession No. NP_063939, CHST7 (2015).
GenBank Accession No. NP_067628, CHST6 (2015).
GenBank Accession No. NP_078809, CHST5 (2015).
GenBank Accession No. Q9Y4C5, CHST2 (2015).
Gessner, J. et al., The IgG Fc receptor family, Annals of Hematology, 76(6):231-248 (1998).
Ghetie, V. and Ward, E., Multiple roles for the major histocompatibility complex class I-related receptor FcRn, Annual Review of Immunology, 18:739-66 (2000).
Grunwell, J. and Bertozzi, C., Carbohydrate sulfotransferases of the GalNAc/Gal/GlcNAc6ST family, Biochemistry, 41(44):13117-13126 (2002).
Hemmerich, S. and Rosen, S., Carbohydrate sulfotransferases in lymphocyte homing. Glycobiology, 10(9):849-856 (2000).
Hinton, P. et al., An engineered human IgG1 antibody with longer serum half-life, Journal of Immunology, 176(1):346-356 (2006).
Idusogie, E. et al., Mapping of the C1q binding site on rituxan, a chimeric antibody with a human IgG1 Fc, Journal of Immunology, 164(8):4178-4184 (2000).
International Search Report for PCT/US13/37997, 3 pages (dated Sep. 9, 2013).
Jassal, R. et al., Sialylation of human IgG-Fc carbohydrate by transfected rat alpha2,6-sialyltransferase, Biochemical and Biophysical Research Communications, 286(2):243-249 (2001).
Jefferis, R. et al., IgG-Fc-mediated effector functions: molecular definition of interaction sites for effector ligands and the role of glycosylation, Immunology Review, 163:59-76 (1998).
Jefferis, Roy, Glycosylation as a strategy to improve antibody-based therapeutics, Nature Reviews Drug Discovery, 8(3):226-234 (2009).
Jefferis, Royston, Criteria for Selection of IgG Isotype and Glycoform of Antibody Therapeutics, BioProcess International, pp. 40-43 (2006).
Lehrnbecher, T. et al., Variant genotypes of the low-affinity Fcgamma receptors in two control populations and a review of low-affinity Fcgamma receptor polymorphisms in control and disease populations, Blood, 94(12):4220-4232 (1999).
Lund, J. et al., Multiple interactions of IgG with its core oligosaccharide can modulate recognition by complement and human Fc gamma receptor I and influence the synthesis of its oligosaccharide chains, Journal of Immunology, 157(11):4963-4969 (1996).
Mattu, T. et al., The glycosylation and structure of human serum IgA1, Fab, and Fc regions and the role of N-glycosylation on Fc? receptor interactions, Journal of Biological Chemistry, 273(4):2260-2272 (1998).
Mimura, Y. et al., Role of oligosaccharide residues of IgG1-Fc in Fc gamma RIIb binding, Journal of Biological Chemistry, 276(49):45539-45547 (2001).
Mizushima, T. et al., Structural basis for improved efficacy of therapeutic antibodies on defucosylation of their Fc glycans, Genes to Cells, 16:1071-1080 (2011).
Moreira, I. et al., Unraveling the importance of protein-protein interaction: application of a computational alanine-scanning mutagenesis to the study of the IgG1 streptococcal protein G (C2 fragment) complex, Journal of Physical Chemistry B, 110(22):10962-10969 (2006).
Nettleton, M. and Kochan, J., Role of glycosylation sites in the IgE Fc molecule, International Archives of Allergy and Immunology, 107(1-3):328-329 (1995).
Patel, A. and Boyd, P., An improved assay for antibody dependent cellular cytotoxicity based on time resolved fluorometry, Journal of Immunological Methods, 184(1):29-38 (1995).
Ravetch, J. and Bolland, S., IgG Fc receptors, Annual Review of Immunology, 19:275-290 (2001).
Rikke, B. and Roy, A., Structural relationships among members of the mammalian sulfotransferase gene family, Biochimica et Biophysica Acta, 1307(3):331-338 (1996).
Salmon, J. et al., Fc gamma receptor IIIb enhances Fc gamma receptor IIa function in an oxidant-dependent and allele-sensitive manner, Journal of Clinical Investigation, 95(6):2877-2885 (1995).
Shields, R. et al., High resolution mapping of the binding site on human IgG1 for Fc gamma RI, Fc gamma RII, Fc gamma RIII, and FcRn and design of IgG1 variants with improved binding to the Fc gamma R, Journal of Biological Chemistry, 276(9):6591-6604 (2001).
Sibéril, S., et al., Molecular aspects of human FcgammaR interactions with IgG: functional and therapeutic consequences, Immunology Letters, 106(2):111-118 (2006).
Stavenhagen, J. et al., Fc optimization of therapeutic antibodies enhances their ability to kill tumor cells in vitro and controls tumor expansion in vivo via low-affinity activating Fcgamma receptors, Cancer Research, 67(18):8882-8890 (2007).
Stewart, R. et al., A variant human IgG1-Fc mediates improved ADCC, Protein Engineering, Design and Select ion, 24(9):671-678 (2011).
Ward E. and Ghetie, V., The effector functions of immunoglobulins: implications for therapy, Therapeutic Immunology, 2(2):77-94 (1995).
Wilkinson, R. et al., Antibody-dependent cell-mediated cytotoxicity: a flow cytometry-based assay using fluorophores, Journal of Immunogical Methods, 258(1-2):183-191 (2001).
Wisecarver, J. et al., A method for determination of antibody-dependent cellular cytotoxicity (ADCC) of human peripheral mononuclear cells, Journal of Immunological Methods, 79(2):277-282 (1985).
Woof, J. et al., Localisation of the monocyte-binding region on human immunoglobulin G, Molecular Immunology, 23(3):319-330 (1986).
Wright, A. and Morrison, S., Effect of glycosylation on antibody function: implications for genetic engineering, Trends in Biotechnology, 15(1):26-32 (1997).
Written Opinion for PCT/US13/37997, 12 pages (dated Sep. 9, 2013).
Zou, G. et al., Chemoenzymatic Synthesis and Fcγ Receptor Binding of Homogeneous Glycoforms of Antibody Fc Domain. Presence of a Bisecting Sugar Moiety Enhances the Affinity of Fc to FcγIIIa Receptor, Journal of the American Chemical Society, 133:18975-18991 (2011).

wt-rituximab

MGWSLILLFLVAVATRVLSQVQLQQPGAELVKPGASVKMSCKASGYTFTSYNM
HWVKQTPGRGLEWIGAIYPGNGDTSYNQKFKGKATLTADKSSSTAYMQLSSLTS
EDSAVYYCARSTYYGGDWYFNVWGAGTTVTVSAASTKGPSVFPLAPSSKSTSG
GTAALGCLVKDYFPEPVTVSWNSGALTSGVHTFPAVLQSSGLYSLSSVVTVPSSS
LGTQTYICNVNHKPSNTKVDKKAEPKSCDKTHTCPPCPAPELLGGPSVFLFPPKP
KDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFFLYSK
LTVDKSRWQQGNVFSCSVMHEALHNHYTQKSLSLSPGK

FIG. 2A mut1- F241A, F243A

MGWSLILLFLVAVATRVLSQVQLQQPGAELVKPGASVKMSCKASGYTFTSYNM
HWVKQTPGRGLEWIGAIYPGNGDTSYNQKFKGKATLTADKSSSTAYMQLSSLTS
EDSAVYYCARSTYYGGDWYFNVWGAGTTVTVSAASTKGPSVFPLAPSSKSTSG
GTAALGCLVKDYFPEPVTVSWNSGALTSGVHTFPAVLQSSGLYSLSSVVTVPSSS
LGTQTYICNVNHKPSNTKVDKKAEPKSCDKTHTCPPCPAPELLGGPSVALAPPKP
KDTLMISRTPEVTCVVVDVSHEDPEVKFNWYVDGVEVHNAKTKPREEQYNSTY
RVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFFLYSK
LTVDKSRWQQGNVFSCSVMHEALHNHYTQKSLSLSPGK

FIG. 2B

| mut2- F243A, R301A |
|---|
| MGWSLILLFLVAVATRVLSQVQLQQPGAELVKPGASVKMSCKASGYTFTSYNM HWVKQTPGRGLEWIGAIYPGNGDTSYNQKFKGKATLTADKSSSTAYMQLSSLTS EDSAVYYCARSTYYGGDWYFNVWGAGTTVTVSAASTKGPSVFPLAPSSKSTSG GTAALGCLVKDYFPEPVTVSWNSGALTSGVHTFPAVLQSSGLYSLSSVVTVPSSS LGTQTYICNVNHKPSNTKVDKKAEPKSCDKTHTCPPCPAPELLGGPSVFLAPPKP KDTLMISRTPEVTCVVVDVSHEDPEVKFNWYVDGVEVHNAKTKPREEQYNSTY AVVSVLTVLHQDWLNGKEYKCKVSNKALPAPIEKTISKAKGQPREPQVYTLPPS RDELTKNQVSLTCLVKGFYPSDIAVEWESNGQPENNYKTTPPVLDSDGSFFLYSK LTVDKSRWQQGNVFSCSVMHEALHNHYTQKSLSLSPGK |

FIG. 2C

| Mut3- K246A, T260A |
|---|
| MGWSLILLFLVAVATRVLSQVQLQQPGAELVKPGASVKMSCKASGYTFTSYNM HWVKQTPGRGLEWIGAIYPGNGDTSYNQKFKGKATLTADKSSSTAYMQLSSLTS EDSAVYYCARSTYYGGDWYFNVWGAGTTVTVSAASTKGPSVFPLAPSSKSTSG GTAALGCLVKDYFPEPVTVSWNSGALTSGVHTFPAVLQSSGLYSLSSVVTVPSSS LGTQTYICNVNHKPSNTKVDKKAEPKSCDKTHTCPPCPAPELLGGPSVFLFPPAP KDTLMISRTPEVACVVVDVSHEDPEVKFNWYVDGVEVHNAKTKPREEQYNSTY RVVSVLTVLHQDWLNGKEYKCKVSNKALPAPIEKTISKAKGQPREPQVYTLPPS RDELTKNQVSLTCLVKGFYPSDIAVEWESNGQPENNYKTTPPVLDSDGSFFLYSK LTVDKSRWQQGNVFSCSVMHEALHNHYTQKSLSLSPGK |

FIG. 2D mut4- T260A, R301A
MGWSLILLFLVAVATRVLSQVQLQQPGAELVKPGASVKMSCKASGYTFTSYNM
HWVKQTPGRGLEWIGAIYPGNGDTSYNQKFKGKATLTADKSSSTAYMQLSSLTS
EDSAVYYCARSTYYGGDWYFNVWGAGTTVTVSAASTKGPSVFPLAPSSKSTSG
GTAALGCLVKDYFPEPVTVSWNSGALTSGVHTFPAVLQSSGLYSLSSVVTVPSSS
LGTQTYICNVNHKPSNTKVDKKAEPKSCDKTHTCPPCPAPELLGGPSVFLFPPKP
KDTLMISRTPEVACVVVDVSHEDPEVKFNWYVDGVEVHNAKTKPREEQYNSTY
AVVSVLTVLHQDWLNGKEYKCKVSNKALPAPIEKTISKAKGQPREPQVYTLPPS
RDELTKNQVSLTCLVKGFYPSDIAVEWESNGQPENNYKTTPPVLDSDGSFFLYSK
LTVDKSRWQQGNVFSCSVMHEALHNHYTQKSLSLSPGK

FIG. 2E

SEQUENCE LISTING

```
<160> NUMBER OF SEQ ID NOS: 5

<210> SEQ ID NO 1
<211> LENGTH: 470
<212> TYPE: PRT
<213> ORGANISM: Homo sapiens

<400> SEQUENCE: 1

Met Gly Trp Ser Leu Ile Leu Leu Phe Leu Val Ala Val Ala Thr Arg
1               5                   10                  15

Val Leu Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
        115                 120                 125

Val Trp Gly Ala Gly Thr Thr Val Thr Val Ser Ala Ala Ser Thr Lys
    130                 135                 140

Gly Pro Ser Val Phe Pro Leu Ala Pro Ser Ser Lys Ser Thr Ser Gly
145                 150                 155                 160
```

```
Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Leu Gly Thr Gln Thr Tyr Ile Cys Asn
    210                 215                 220

Val Asn His Lys Pro Ser Asn Thr Lys Val Asp Lys Lys Ala Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430

Leu Thr Val Asp Lys Ser Arg Trp Gln Gln Gly Asn Val Phe Ser Cys
        435                 440                 445

Ser Val Met His Glu Ala Leu His Asn His Tyr Thr Gln Lys Ser Leu
    450                 455                 460

Ser Leu Ser Pro Gly Lys
465                 470

<210> SEQ ID NO 2
<211> LENGTH: 470
<212> TYPE: PRT
<213> ORGANISM: Homo sapiens
<220> FEATURE:
<221> NAME/KEY: MISC_FEATURE
<222> LOCATION: (264)..(264)
<223> OTHER INFORMATION: F241A
<220> FEATURE:
<221> NAME/KEY: MISC_FEATURE
<222> LOCATION: (266)..(266)
<223> OTHER INFORMATION: F243A

<400> SEQUENCE: 2

Met Gly Trp Ser Leu Ile Leu Leu Phe Leu Val Ala Val Ala Thr Arg
1               5                   10                  15
```

```
Val Leu Ser Gln Val Gln Leu Gln Gln Pro Gly Ala Glu Leu Val Lys
                20                  25                  30

Pro Gly Ala Ser Val Lys Met Ser Cys Lys Ala Ser Gly Tyr Thr Phe
            35                  40                  45

Thr Ser Tyr Asn Met His Trp Val Lys Gln Thr Pro Gly Arg Gly Leu
 50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
        115                 120                 125

Val Trp Gly Ala Gly Thr Thr Val Thr Val Ser Ala Ala Ser Thr Lys
130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
        210                 215                 220

Val Asn His Lys Pro Ser Asn Thr Lys Val Asp Lys Lys Ala Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Ala Leu Ala Pro Pro Lys Pro Lys Asp
            260                 265                 270

Thr Leu Met Ile Ser Arg Thr Pro Glu Val Thr Cys Val Val Val Asp
        275                 280                 285

Val Ser His Glu Asp Pro Glu Val Lys Phe Asn Trp Tyr Val Asp Gly
        290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
            340                 345                 350

Ala Pro Ile Glu Lys Thr Ile Ser Lys Ala Lys Gly Gln Pro Arg Glu
        355                 360                 365

Pro Gln Val Tyr Thr Leu Pro Pro Ser Arg Asp Glu Leu Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
            420                 425                 430
```

```
Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
    450                 455                 460

Ser Leu Ser Pro Gly Lys
465             470

<210> SEQ ID NO 3
<211> LENGTH: 470
<212> TYPE: PRT
<213> ORGANISM: Homo sapiens
<220> FEATURE:
<221> NAME/KEY: MISC_FEATURE
<222> LOCATION: (266)..(266)
<223> OTHER INFORMATION: F243A
<220> FEATURE:
<221> NAME/KEY: MISC_FEATURE
<222> LOCATION: (324)..(324)
<223> OTHER INFORMATION: R301A

<400> SEQUENCE: 3

Met Gly Trp Ser Leu Ile Leu Leu Phe Leu Val Ala Val Ala Thr Arg
1               5                   10                  15

Val Leu Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
            100                 105                 110

Tyr Tyr Cys Ala Arg Ser Thr Tyr Tyr Gly Gly Asp Trp Tyr Phe Asn
        115                 120                 125

Val Trp Gly Ala Gly Thr Thr Val Thr Val Ser Ala Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
            180                 185                 190

Phe Pro Ala Val Leu Gln Ser Ser Gly Leu Tyr Ser Leu Ser Ser Val
        195                 200                 205

Val Thr Val Pro Ser Ser Ser Leu Gly Thr Gln Thr Tyr Ile Cys Asn
    210                 215                 220

Val Asn His Lys Pro Ser Asn Thr Lys Val Asp Lys Lys Ala Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Ala Pro Pro Lys Pro Lys Asp
            260                 265                 270

Thr Leu Met Ile Ser Arg Thr Pro Glu Val Thr Cys Val Val Val Asp
        275                 280                 285
```

```
Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Arg Val Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
                355                 360                 365

Pro Gln Val Tyr Thr Leu Pro Pro Ser Arg Asp Glu Leu Thr Lys Asn
        370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
                420                 425                 430

Leu Thr Val Asp Lys Ser Arg Trp Gln Gln Gly Asn Val Phe Ser Cys
                435                 440                 445

Ser Val Met His Glu Ala Leu His Asn His Tyr Thr Gln Lys Ser Leu
                450                 455                 460

Ser Leu Ser Pro Gly Lys
465                 470

<210> SEQ ID NO 4
<211> LENGTH: 470
<212> TYPE: PRT
<213> ORGANISM: Homo sapiens
<220> FEATURE:
<221> NAME/KEY: MISC_FEATURE
<222> LOCATION: (269)..(269)
<223> OTHER INFORMATION: K246A
<220> FEATURE:
<221> NAME/KEY: MISC_FEATURE
<222> LOCATION: (283)..(283)
<223> OTHER INFORMATION: T260A

<400> SEQUENCE: 4

Met Gly Trp Ser Leu Ile Leu Leu Phe Leu Val Ala Val Ala Thr Arg
1               5                   10                  15

Val Leu Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
        35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
                100                 105                 110

Tyr Tyr Cys Ala Arg Ser Thr Tyr Tyr Gly Gly Asp Trp Tyr Phe Asn
            115                 120                 125

Val Trp Gly Ala Gly Thr Thr Val Thr Val Ser Ala Ala Ser Thr Lys
        130                 135                 140
```

```
Gly Pro Ser Val Phe Pro Leu Ala Pro Ser Ser Lys Ser Thr Ser Gly
145                 150                 155                 160
Gly Thr Ala Ala Leu Gly Cys Leu Val Lys Asp Tyr Phe Pro Glu Pro
                165                 170                 175
Val Thr Val Ser Trp Asn Ser Gly Ala Leu Thr Ser Gly Val His Thr
            180                 185                 190
Phe Pro Ala Val Leu Gln Ser Ser Gly Leu Tyr Ser Leu Ser Ser Val
        195                 200                 205
Val Thr Val Pro Ser Ser Ser Leu Gly Thr Gln Thr Tyr Ile Cys Asn
    210                 215                 220
Val Asn His Lys Pro Ser Asn Thr Lys Val Asp Lys Lys Ala Glu Pro
225                 230                 235                 240
Lys Ser Cys Asp Lys Thr His Thr Cys Pro Pro Cys Pro Ala Pro Glu
                245                 250                 255
Leu Leu Gly Gly Pro Ser Val Phe Leu Phe Pro Pro Ala Pro Lys Asp
            260                 265                 270
Thr Leu Met Ile Ser Arg Thr Pro Glu Val Ala Cys Val Val Val Asp
        275                 280                 285
Val Ser His Glu Asp Pro Glu Val Lys Phe Asn Trp Tyr Val Asp Gly
    290                 295                 300
Val Glu Val His Asn Ala Lys Thr Lys Pro Arg Glu Glu Gln Tyr Asn
305                 310                 315                 320
Ser Thr Tyr Arg Val Val Ser Val Leu Thr Val Leu His Gln Asp Trp
                325                 330                 335
Leu Asn Gly Lys Glu Tyr Lys Cys Lys Val Ser Asn Lys Ala Leu Pro
            340                 345                 350
Ala Pro Ile Glu Lys Thr Ile Ser Lys Ala Lys Gly Gln Pro Arg Glu
        355                 360                 365
Pro Gln Val Tyr Thr Leu Pro Pro Ser Arg Asp Glu Leu Thr Lys Asn
    370                 375                 380
Gln Val Ser Leu Thr Cys Leu Val Lys Gly Phe Tyr Pro Ser Asp Ile
385                 390                 395                 400
Ala Val Glu Trp Glu Ser Asn Gly Gln Pro Glu Asn Asn Tyr Lys Thr
                405                 410                 415
Thr Pro Pro Val Leu Asp Ser Asp Gly Ser Phe Phe Leu Tyr Ser Lys
            420                 425                 430
Leu Thr Val Asp Lys Ser Arg Trp Gln Gln Gly Asn Val Phe Ser Cys
        435                 440                 445
Ser Val Met His Glu Ala Leu His Asn His Tyr Thr Gln Lys Ser Leu
    450                 455                 460
Ser Leu Ser Pro Gly Lys
465                 470

<210> SEQ ID NO 5
<211> LENGTH: 470
<212> TYPE: PRT
<213> ORGANISM: Homo sapiens
<220> FEATURE:
<221> NAME/KEY: MISC_FEATURE
<222> LOCATION: (283)..(283)
<223> OTHER INFORMATION: T260A
<220> FEATURE:
<221> NAME/KEY: MISC_FEATURE
<222> LOCATION: (324)..(324)
<223> OTHER INFORMATION: R301A

<400> SEQUENCE: 5
```

```
Met Gly Trp Ser Leu Ile Leu Leu Phe Leu Val Ala Val Ala Thr Arg
1               5                   10                  15

Val Leu Ser Gln Val Gln Leu Gln Gln Pro Gly Ala Glu Leu Val Lys
            20                  25                  30

Pro Gly Ala Ser Val Lys Met Ser Cys Lys Ala Ser Gly Tyr Thr Phe
            35                  40                  45

Thr Ser Tyr Asn Met His Trp Val Lys Gln Thr Pro Gly Arg Gly Leu
    50                  55                  60

Glu Trp Ile Gly Ala Ile Tyr Pro Gly Asn Gly Asp Thr Ser Tyr Asn
65                  70                  75                  80

Gln Lys Phe Lys Gly Lys Ala Thr Leu Thr Ala Asp Lys Ser Ser Ser
                85                  90                  95

Thr Ala Tyr Met Gln Leu Ser Ser Leu Thr Ser Glu Asp Ser Ala Val
                100                 105                 110

Tyr Tyr Cys Ala Arg Ser Thr Tyr Tyr Gly Gly Asp Trp Tyr Phe Asn
            115                 120                 125

Val Trp Gly Ala Gly Thr Thr Val Thr Val Ser Ala Ala Ser Thr Lys
    130                 135                 140

Gly Pro Ser Val Phe Pro Leu Ala Pro Ser Ser Lys Ser Thr Ser Gly
145                 150                 155                 160

Gly Thr Ala Ala Leu Gly Cys Leu Val Lys Asp Tyr Phe Pro Glu Pro
                165                 170                 175

Val Thr Val Ser Trp Asn Ser Gly Ala Leu Thr Ser Gly Val His Thr
                180                 185                 190

Phe Pro Ala Val Leu Gln Ser Ser Gly Leu Tyr Ser Leu Ser Ser Val
            195                 200                 205

Val Thr Val Pro Ser Ser Ser Leu Gly Thr Gln Thr Tyr Ile Cys Asn
210                 215                 220

Val Asn His Lys Pro Ser Asn Thr Lys Val Asp Lys Lys Ala Glu Pro
225                 230                 235                 240

Lys Ser Cys Asp Lys Thr His Thr Cys Pro Pro Cys Pro Ala Pro Glu
                245                 250                 255

Leu Leu Gly Gly Pro Ser Val Phe Leu Phe Pro Pro Lys Pro Lys Asp
                260                 265                 270

Thr Leu Met Ile Ser Arg Thr Pro Glu Val Ala Cys Val Val Val Asp
            275                 280                 285

Val Ser His Glu Asp Pro Glu Val Lys Phe Asn Trp Tyr Val Asp Gly
    290                 295                 300

Val Glu Val His Asn Ala Lys Thr Lys Pro Arg Glu Glu Gln Tyr Asn
305                 310                 315                 320

Ser Thr Tyr Ala Val Ser Val Leu Thr Val Leu His Gln Asp Trp
                325                 330                 335

Leu Asn Gly Lys Glu Tyr Lys Cys Lys Val Ser Asn Lys Ala Leu Pro
                340                 345                 350

Ala Pro Ile Glu Lys Thr Ile Ser Lys Ala Lys Gly Gln Pro Arg Glu
            355                 360                 365

Pro Gln Val Tyr Thr Leu Pro Pro Ser Arg Asp Glu Leu Thr Lys Asn
    370                 375                 380

Gln Val Ser Leu Thr Cys Leu Val Lys Gly Phe Tyr Pro Ser Asp Ile
385                 390                 395                 400

Ala Val Glu Trp Glu Ser Asn Gly Gln Pro Glu Asn Asn Tyr Lys Thr
                405                 410                 415

Thr Pro Pro Val Leu Asp Ser Asp Gly Ser Phe Phe Leu Tyr Ser Lys
```

-continued

```
            420                 425                 430
Leu Thr Val Asp Lys Ser Arg Trp Gln Gln Gly Asn Val Phe Ser Cys
            435                 440                 445

Ser Val Met His Glu Ala Leu His Asn His Tyr Thr Gln Lys Ser Leu
    450                 455                 460

Ser Leu Ser Pro Gly Lys
465                 470
```

MODIFIED GLYCOPROTEINS

CROSS REFERENCE TO RELATED APPLICATIONS

This application is a continuation of U.S. application Ser. No. 14/396,420, filed on Oct. 23, 2014, which is the National Stage of International Application No. PCT/US2013/037997, filed on Apr. 24, 2013, which claims the benefit of U.S. Provisional Application No. 61/638,099, filed on Apr. 25, 2012, the contents of all of which are herein incorporated by reference in their entirety.

REFERENCE TO SEQUENCE LISTING

The specification includes a Sequence Listing in the form of an ASCII compliant text file named "Sequence_Listing.txt", which was created on May 15, 2013 and has a size of 21 kilobytes. The entire contents of the Sequence Listing are herein incorporated by reference.

FIELD OF THE INVENTION

The invention relates generally to glycobiology and glycoproteins.

BACKGROUND

Therapeutic glycoproteins are an important class of therapeutic biotechnology products, and therapeutic antibodies (including murine, chimeric, humanized and human antibodies and fragments thereof) account for the majority of therapeutic biologic products.

SUMMARY

The invention is based, in part, on the discovery that modifications of the amino acid sequence of glycoproteins, e.g., glycoproteins having all or a portion of an immunoglobulin Fc region, result in modified glycan composition on the glycoprotein, and can affect its activity and/or function. Accordingly, the invention features glycoproteins (e.g., antibodies or Fc-receptor fusion proteins) that include a modified immunoglobulin Fc region, as well as methods of making them, and methods of using them.

In one aspect, the invention features a modified glycoprotein comprising a modified amino acid sequence of a reference glycoprotein and comprising a modified glycan, wherein the reference glycoprotein comprises an immunoglobulin Fc region, or Fc fragment, comprising a reference glycan, wherein the modified glycoprotein comprises one or more amino acid substitutions of the Fc region, or Fc fragment, of the reference glycoprotein. In some embodiments, the one or more amino acid substitutions result in increased sulfation of the modified glycan relative to the reference glycan.

In some embodiments, at least one of the amino acids substituted is F241, F243, K246, T260, or R301 of an IgG heavy chain. In some embodiments, at least one of the amino acid substitutions is F241A, F243A, K246A, T260A, or R301A.

In some embodiments, the modified glycoprotein comprises two or more amino acid substitutions of the Fc region, or Fc fragment, of the reference glycoprotein. In some embodiments, the two or more amino acid substitutions result in increased sulfation of the modified glycan relative to the reference glycan. In some embodiments, at least two of the amino acid substitutions are selected from F241A, F243A, K246A, T260A, and R301A. In particular embodiments, at least two of the amino acid substitutions are F241A and F243A; F241A and K246A; F241A and T260A; F241A and R301A; F243A and K246A; F243A and T260A; F243A and R301A; K246A and T260A; K246A and R301A; or T260A and R301A.

In some embodiments, the modified glycan has an altered glycan composition (e.g., an altered glycan composition described herein) relative to the reference glycan. In some embodiments, the modified glycan has an altered (e.g., increased or decreased) level of sialylation (e.g., alpha-2,6 or alpha-2,3 linked sialylation) relative to the reference glycan. In some embodiments, the modified glycan has an altered (e.g., increased or decreased) level of fucosylation (e.g., antennary fucosylation) relative to the reference glycan. In some embodiments, the modified glycan has an altered (e.g., increased or decreased) level of bisecting N-acetylglucosamine relative to the reference glycan.

In some embodiments, the level of sialylation, fucosylation, and/or bisecting N-acetylglucosamine in the modified glycan is increased by about 10%, about 20%, about 30%, about 40%, about 50%, about 60%, about 70%, about 80%, about 90%, about 100%, about 125%, about 150%, about 175%, about 200%, about 300%, about 400%, about 500%, or more, relative to the level in the reference glycan.

In other embodiments, the level of sialylation, fucosylation, and/or bisecting N-acetylglucosamine in the modified glycan is decreased by about 10%, about 20%, about 30%, about 40%, about 50%, about 60%, about 70%, about 80%, about 90%, about 100%, about 125%, about 150%, about 175%, about 200%, about 300%, about 400%, about 500%, or more, relative to the level in the reference glycan.

In some embodiments, the modified glycoprotein is sulfated. In some embodiments, the modified glycoprotein comprises a modified glycan that is sulfated at a higher level relative to the reference glycan.

In some embodiments, the modified glycoprotein has an altered activity (e.g., an altered activity described herein) relative to the reference glycoprotein. In some embodiments, the modified glycoprotein has a different, e.g., a detectably higher or lower, activity, such as an immune cell activating activity, e.g., Fc receptor affinity, Fc receptor specificity, complement activation activity, signaling activity, targeting activity, effector function, half-life, clearance, pro-inflammatory, anti-inflammatory, or transcytosis activity than the reference glycoprotein. In some embodiments, the effector function is antibody dependent cellular cytotoxicity, complement dependent cytotoxicity, programmed cell death, or cellular phagocytosis.

In certain embodiments, the Fc receptor is an FcγRI, FCγRIIA, FcγRIIB, FcγRIIIA, FcγRIIIB, FcγRIV, or FcRn receptor. In particular embodiments, the glycoprotein binds to an immune cell, e.g., a macrophage, neutrophil, dendritic cell, B cell, natural killer cell (NKC), or eosinophil.

In some embodiments, the reference glycoprotein is a reference antibody. In certain embodiments, the reference antibody is an IgA, IgD, IgE, IgG, or IgM antibody. In particular embodiments, the reference antibody is an IgG1, IgG2, or IgG3 antibody.

In certain embodiments, the reference antibody is abciximab, adalimumab, alemtuzumab, basiliximab, bevacizumab, cetuximab, certolizumab, daclizumab, eculizumab, efalizumab, gemtuzumab, ibritumomab, infliximab, muromonab, natalizumab, omalizumab, palivizumab, panitumumab, ranibizumab, rituximab, tositumomab, or trastuzumab.

In yet other embodiments, the reference glycoprotein is conjugated to a heterologous moiety. In some embodiments, the heterologous moiety is a polypeptide, nucleic acid, or small molecule. In particular embodiments, the reference glycoprotein is alefacept, abatacept, etanercept, rilonacept, or denileukin diftitox.

In some embodiments, the modified glycoprotein comprises two Fc regions, wherein one of the Fc regions comprises one or more amino acid substitutions, e.g., one or more amino acid substitutions described herein. In other embodiments, the modified glycoprotein comprises two Fc regions, wherein both Fc regions comprise one or more amino acid substitutions, e.g., one or more amino acid substitutions described herein.

In another aspect, the invention features a modified glycoprotein comprising a modified amino acid sequence of a reference glycoprotein, wherein the reference glycoprotein comprises an immunoglobulin Fc region, or Fc fragment, wherein the modified glycoprotein comprises two or more amino acid substitutions of the Fc region, or Fc fragment, of the reference glycoprotein, and wherein at least one of the amino acids substituted is F241, F243, K246, T260, or R301 of an IgG heavy chain.

In some embodiments, at least one of the amino acid substitutions is F241A, F243A, K246A, T260A, or R301A.

In some embodiments, at least two of the amino acid substitutions are selected from F241A, F243A, K246A, T260A, and R301A. In particular embodiments, at least two of the amino acid substitutions are F241A and F243A; F241A and K246A; F241A and T260A; F241A and R301A; F243A and K246A; F243A and T260A; F243A and R301A; K246A and T260A; K246A and R301A; or T260A and R301A.

In some embodiments, the reference glycoprotein comprises a reference glycan, and the modified glycoprotein comprises a modified glycan having an altered composition relative to the reference glycan. In some embodiments, the modified glycan has an altered (e.g., increased or decreased) level of sialylation (e.g., alpha-2,6 or alpha-2,3 linked sialylation) relative to the reference glycan. In some embodiments, the modified glycan has an altered (e.g., increased or decreased) level of fucosylation (e.g., antennary fucosylation) relative to the reference glycan. In some embodiments, the modified glycan has an altered (e.g., increased or decreased) level of bisecting N-acetylglucosamine relative to the reference glycan.

In some embodiments, the level of sialylation, fucosylation, and/or bisecting N-acetylglucosamine in the modified glycan is increased by about 10%, about 20%, about 30%, about 40%, about 50%, about 60%, about 70%, about 80%, about 90%, about 100%, about 125%, about 150%, about 175%, about 200%, about 300%, about 400%, about 500%, or more, relative to the level in the reference glycan.

In other embodiments, the level of sialylation, fucosylation, and/or bisecting N-acetylglucosamine in the modified glycan is decreased by about 10%, about 20%, about 30%, about 40%, about 50%, about 60%, about 70%, about 80%, about 90%, about 100%, about 125%, about 150%, about 175%, about 200%, about 300%, about 400%, about 500%, or more, relative to the level in the reference glycan.

In some embodiments, the two or more amino acid substitutions result in increased sulfation of the modified glycan relative to the reference glycan.

In some embodiments, the modified glycoprotein has an altered activity (e.g., an altered activity described herein) relative to the reference glycoprotein. In some embodiments, the modified glycoprotein has a different, e.g., a detectably higher or lower, activity, such as an immune cell activating activity, e.g., Fc receptor affinity, Fc receptor specificity, complement activation activity, signaling activity, targeting activity, effector function, half-life, clearance, pro-inflammatory, anti-inflammatory, or transcytosis activity than a corresponding glycoprotein without the substituted amino acids. In some embodiments, the effector function is antibody dependent cellular cytotoxicity, complement dependent cytotoxicity, programmed cell death, or cellular phagocytosis.

In certain embodiments, the Fc receptor is an FcγRI, FcγRIIA, FcγRIIB, FcγRIIIA, FcγRIIIB FcγRIV, or FcRn receptor. In particular embodiments, the glycoprotein binds to an immune cell, e.g., a macrophage, neutrophil, dendritic cell, B cell, natural killer cell (NKC), or eosinophil.

In some embodiments, the reference glycoprotein is a reference antibody. In certain embodiments, the reference antibody is an IgA, IgD, IgE, IgG, or IgM antibody. In particular embodiments, the reference antibody is an IgG1, IgG2, or IgG3 antibody.

In certain embodiments, the reference antibody is abciximab, adalimumab, alemtuzumab, basiliximab, bevacizumab, cetuximab, certolizumab, daclizumab, eculizumab, efalizumab, gemtuzumab, ibritumomab, infliximab, muromonab, natalizumab, omalizumab, palivizumab, panitumumab, ranibizumab, rituximab, tositumomab, or trastuzumab.

In yet other embodiments, the reference glycoprotein is conjugated to a heterologous moiety. In some embodiments, the heterologous moiety is a polypeptide, nucleic acid, or small molecule. In particular embodiments, the reference glycoprotein is alefacept, abatacept, etanercept, rilonacept, or denileukin diftitox.

In some embodiments, the modified glycoprotein comprises two Fc regions, wherein one of the Fc regions comprises one or more amino acid substitutions, e.g., one or more amino acid substitutions described herein. In other embodiments, the modified glycoprotein comprises two Fc regions, wherein both Fc regions comprise one or more amino acid substitutions, e.g., one or more amino acid substitutions described herein.

In another aspect, the invention features a modified glycoprotein comprising a modified amino acid sequence of a reference glycoprotein, wherein the reference glycoprotein comprises an IgG1 immunoglobulin Fc region, or Fc fragment, comprising a glycan, wherein the modified glycoprotein comprises at least one amino acid substitution of the Fc region, or Fc fragment, of the reference glycoprotein, and wherein at least one of the amino acids substituted is F241 or F243 of an IgG heavy chain.

In some embodiments, at least one of the amino acid substitutions is F241A or F243A. In other embodiments, the modified glycoprotein comprises at least two amino acid substitutions comprising F241A and F243A.

In some embodiments, the modified glycan has an altered glycan composition (e.g., an altered glycan composition described herein) relative to the reference glycan. In some embodiments, the modified glycan has an altered (e.g., increased or decreased) level of sialylation (e.g., alpha-2,6 or alpha-2,3 linked sialylation) relative to the reference glycan. In some embodiments, the modified glycan has an altered (e.g., increased or decreased) level of fucosylation (e.g., antennary fucosylation) relative to the reference glycan. In some embodiments, the modified glycan has an altered (e.g., increased or decreased) level of bisecting N-acetylglucosamine relative to the reference glycan.

In some embodiments, the level of sialylation, fucosylation, and/or bisecting N-acetylglucosamine in the modified glycan is increased by about 10%, about 20%, about 30%, about 40%, about 50%, about 60%, about 70%, about 80%, about 90%, about 100%, about 125%, about 150%, about 175%, about 200%, about 300%, about 400%, about 500%, or more, relative to the level in the reference glycan.

In other embodiments, the level of sialylation, fucosylation, and/or bisecting N-acetylglucosamine in the modified glycan is decreased by about 10%, about 20%, about 30%, about 40%, about 50%, about 60%, about 70%, about 80%, about 90%, about 100%, about 125%, about 150%, about 175%, about 200%, about 300%, about 400%, about 500%, or more, relative to the level in the reference glycan.

In some embodiments, the modified glycoprotein is sulfated. In some embodiments, the modified glycoprotein comprises a modified glycan that is sulfated at a higher level relative to the reference glycan.

In some embodiments, the modified glycoprotein has an altered activity (e.g., an altered activity described herein) relative to the reference glycoprotein. In some embodiments, the modified glycoprotein has a different, e.g., a detectably higher or lower, activity, such as an immune cell activating activity, e.g., Fc receptor affinity, Fc receptor specificity, complement activation activity, signaling activity, targeting activity, effector function, half-life, clearance, pro-inflammatory, anti-inflammatory, or transcytosis activity than a corresponding glycoprotein without the substituted amino acids. In some embodiments, the effector function is antibody dependent cellular cytotoxicity, complement dependent cytotoxicity, programmed cell death, or cellular phagocytosis.

In certain embodiments, the Fc receptor is an FcγRI, FcγRIIA, FcγRIIB, FcγRITTA, FcγRIIIB FcγRIV, or FcRn receptor. In particular embodiments, the glycoprotein binds to an immune cell, e.g., a macrophage, neutrophil, dendritic cell, B cell, natural killer cell (NKC), or eosinophil.

In some embodiments, the reference glycoprotein is a reference antibody. In certain embodiments, the reference antibody is an IgA, IgD, IgE, IgG, or IgM antibody. In particular embodiments, the reference antibody is an IgG1, IgG2, or IgG3 antibody.

In certain embodiments, the reference antibody is abciximab, adalimumab, alemtuzumab, basiliximab, bevacizumab, cetuximab, certolizumab, daclizumab, eculizumab, efalizumab, gemtuzumab, ibritumomab, infliximab, muromonab, natalizumab, omalizumab, palivizumab, panitumumab, ranibizumab, rituximab, tositumomab, or trastuzumab.

In yet other embodiments, the reference glycoprotein is conjugated to a heterologous moiety. In some embodiments, the heterologous moiety is a polypeptide, nucleic acid, or small molecule. In particular embodiments, the reference glycoprotein is alefacept, abatacept, etanercept, rilonacept, or denileukin diftitox.

In some embodiments, the modified glycoprotein comprises two Fc regions, wherein one of the Fc regions comprises one or more amino acid substitutions, e.g., one or more amino acid substitutions described herein. In other embodiments, the modified glycoprotein comprises two Fc regions, wherein both Fc regions comprise one or more amino acid substitutions, e.g., one or more amino acid substitutions described herein.

In another aspect, the invention features a method of selectively targeting a modified glycoprotein to a cell or tissue. The method comprises: providing a modified glycoprotein comprising a modified amino acid sequence of a reference glycoprotein and comprising a modified glycan, wherein the reference glycoprotein comprises an immunoglobulin Fc region, or Fc fragment, comprising a reference glycan, wherein the modified glycoprotein comprises one or more amino acid substitutions of the Fc region, or fragment, of the reference glycoprotein; and contacting the modified glycoprotein with a cell or tissue comprising a target Fc receptor, thereby selectively targeting the modified glycoprotein to the cell or tissue. In some embodiments, the one or more amino acid substitutions result in increased sulfation of the modified glycan relative to the reference glycan.

In some embodiments, at least one of the amino acids substituted is F241, F243, K246, T260, or R301 of an IgG heavy chain. In some embodiments, at least one of the amino acid substitutions is F241A, F243A, K246A, T260A, or R301A.

In some embodiments, the modified glycoprotein comprises two or more amino acid substitutions of the Fc region, or Fc fragment, of the reference glycoprotein, wherein the two or more amino acid substitutions result in increased sulfation of the modified glycan relative to the reference glycan. In some embodiments, at least two of the amino acid substitutions are selected from F241A, F243A, K246A, T260A, and R301A. In particular embodiments, at least two of the amino acid substitutions are F241A and F243A; F241A and K246A; F241A and T260A; F241A and R301A; F243A and K246A; F243A and T260A; F243A and R301A; K246A and T260A; K246A and R301A; or T260A and R301A.

In some embodiments, the modified glycan has an altered glycan composition (e.g., an altered glycan composition described herein) relative to the reference glycan. In some embodiments, the modified glycan has an altered (e.g., increased or decreased) level of sialylation (e.g., alpha-2,6 or alpha-2,3 linked sialylation) relative to the reference glycan. In some embodiments, the modified glycan has an altered (e.g., increased or decreased) level of fucosylation (e.g., antennary fucosylation) relative to the reference glycan. In some embodiments, the modified glycan has an altered (e.g., increased or decreased) level of bisecting N-acetylglucosamine relative to the reference glycan.

In some embodiments, the level of sialylation, fucosylation, and/or bisecting N-acetylglucosamine in the modified glycan is increased by about 10%, about 20%, about 30%, about 40%, about 50%, about 60%, about 70%, about 80%, about 90%, about 100%, about 125%, about 150%, about 175%, about 200%, about 300%, about 400%, about 500%, or more, relative to the level in the reference glycan.

In other embodiments, the level of sialylation, fucosylation, and/or bisecting N-acetylglucosamine in the modified glycan is decreased by about 10%, about 20%, about 30%, about 40%, about 50%, about 60%, about 70%, about 80%, about 90%, about 100%, about 125%, about 150%, about 175%, about 200%, about 300%, about 400%, about 500%, or more, relative to the level in the reference glycan.

In some embodiments, the modified glycoprotein is sulfated. In some embodiments, the modified glycoprotein comprises a modified glycan that is sulfated at a higher level relative to the reference glycan.

In some embodiments, the modified glycoprotein has an altered activity (e.g., an altered activity described herein) relative to the reference glycoprotein. In some embodiments, the modified glycoprotein has a different, e.g., a detectably higher or lower, activity, such as an immune cell activating activity, e.g., Fc receptor affinity, Fc receptor specificity, complement activation activity, signaling activity, targeting activity, effector function, half-life, clearance, pro-inflammatory, anti-inflammatory, or transcytosis activity than a corresponding glycoprotein without the substituted amino acids. In some embodiments, the effector function is antibody dependent cellular cytotoxicity, complement dependent cytotoxicity, programmed cell death, or cellular phagocytosis.

In certain embodiments, the Fc receptor is an FcγRI, FcγRIIA, FcγRIIB, FcγRIIIA, FcγRIIIB FcγRIV, or FcRn receptor. In particular embodiments, the glycoprotein binds to an immune cell, e.g., a macrophage, neutrophil, dendritic cell, B cell, natural killer cell (NKC), or eosinophil.

In some embodiments, the reference glycoprotein is a reference antibody. In certain embodiments, the reference antibody is an IgA, IgD, IgE, IgG, or IgM antibody. In particular embodiments, the reference antibody is an IgG1, IgG2, or IgG3 antibody.

In certain embodiments, the reference antibody is abciximab, adalimumab, alemtuzumab, basiliximab, bevacizumab, cetuximab, certolizumab, daclizumab, eculizumab, efalizumab, gemtuzumab, ibritumomab, infliximab, muromonab, natalizumab, omalizumab, palivizumab, panitumumab, ranibizumab, rituximab, tositumomab, or trastuzumab.

In yet other embodiments, the reference glycoprotein is conjugated to a heterologous moiety. In some embodiments, the heterologous moiety is a polypeptide, nucleic acid, or small molecule. In particular embodiments, the reference glycoprotein is alcfacept, abatacept, etanercept, rilonacept, or denileukin diftitox.

In some embodiments, the modified glycoprotein comprises two Fc regions, wherein one of the Fc regions comprises one or more amino acid substitutions, e.g., one or more amino acid substitutions described herein. In other embodiments, the modified glycoprotein comprises two Fc regions, wherein both Fc regions comprise one or more amino acid substitutions, e.g., one or more amino acid substitutions described herein.

In another aspect, the invention features a method of producing a modified glycoprotein. The method comprises expressing in a cell a recombinant modified glycoprotein comprising a modified amino acid sequence of a reference glycoprotein and comprising a modified glycan, wherein the reference glycoprotein comprises an immunoglobulin Fc region, or Fc fragment, comprising a reference glycan, wherein the modified glycoprotein comprises one or more amino acid substitutions of the Fc region, or Fc fragment, of the reference glycoprotein; and purifying the modified glycoprotein. In some embodiments, the one or more amino acid substitutions result in increased sulfation of the modified glycan relative to the reference glycan.

In some embodiments, the cell is genetically engineered to express one or more exogenous glycosylation enzymes, e.g., one or more glycosyltransferase, e.g., one or more glycosyltransferase described herein. In other embodiments, the cell is genetically engineered to over-express or under-express an endogenous glycosylation enzyme, e.g., one or more endogenous glycosyltransferases, e.g., one or more endogenous glycosyltransferases described herein.

In some embodiments, at least one of the amino acids substituted is F241, F243, K246, T260, or R301 of an IgG heavy chain. In some embodiments, at least one of the amino acid substitutions is F241A, F243A, K246A, T260A, or R301A.

In some embodiments, the modified glycoprotein comprises two or more amino acid substitutions of the Fc region, or Fc fragment, of the reference glycoprotein, wherein the two or more amino acid substitutions result in increased sulfation of the modified glycan relative to the reference glycan. In some embodiments, at least two of the amino acid substitutions are selected from F241A, F243A, K246A, T260A, and R301A. In particular embodiments, at least two of the amino acid substitutions are F241A and F243A; F241A and K246A; F241A and T260A; F241A and R301A; F243A and K246A; F243A and T260A; F243A and R301A; K246A and T260A; K246A and R301A; or T260A and R301A.

In some embodiments, the modified glycan has an altered glycan composition (e.g., an altered glycan composition described herein) relative to the reference glycan. In some embodiments, the modified glycan has an altered (e.g., increased or decreased) level of sialylation (e.g., alpha-2,6 or alpha-2,3 linked sialylation) relative to the reference glycan. In some embodiments, the modified glycan has an altered (e.g., increased or decreased) level of fucosylation (e.g., antennmy fucosylation) relative to the reference glycan. In some embodiments, the modified glycan has an altered (e.g., increased or decreased) level of bisecting N-acetylglucosamine relative to the reference glycan.

In some embodiments, the level of sialylation, fucosylation, and/or bisecting N-acetylglucosamine in the modified glycan is increased by about 10%, about 20%, about 30%, about 40%, about 50%, about 60%, about 70%, about 80%, about 90%, about 100%, about 125%, about 150%, about 175%, about 200%, about 300%, about 400%, about 500%, or more, relative to the level in the reference glycan.

In other embodiments, the level of sialylation, fucosylation, and/or bisecting N-acetylglucosamine in the modified glycan is decreased by about 10%, about 20%, about 30%, about 40%, about 50%, about 60%, about 70%, about 80%, about 90%, about 100%, about 125%, about 150%, about 175%, about 200%, about 300%, about 400%, about 500%, or more, relative to the level in the reference glycan.

In some embodiments, the modified glycoprotein is sulfated. In some embodiments, the modified glycoprotein comprises a modified glycan that is sulfated at a higher level relative to the reference glycan.

In some embodiments, the modified glycoprotein has an altered activity (e.g., an altered activity described herein) relative to the reference glycoprotein. In some embodiments, the modified glycoprotein has a different, e.g., a detectably higher or lower, activity, such as an immune cell activating activity, e.g., Fc receptor affinity, Fc receptor specificity, complement activation activity, signaling activity, targeting activity, effector function, half-life, clearance, pro-inflammatory, anti-inflammatory, or transcytosis activity than a corresponding glycoprotein without the substituted amino acids. In some embodiments, the effector function is antibody dependent cellular cytotoxicity, complement dependent cytotoxicity, programmed cell death, or cellular phagocytosis.

In certain embodiments, the Fc receptor is an FcγRI, FcγRIIA, FcγRIIB, FcγRIIIA, FcγRIIIB FcγRIV, or FcRn receptor. In particular embodiments, the glycoprotein binds to an immune cell, e.g., a macrophage, neutrophil, dendritic cell, B cell, natural killer cell (NKC), or eosinophil.

In some embodiments, the reference glycoprotein is a reference antibody. In certain embodiments, the reference antibody is an lgA, lgD, IgE, IgG, or lgM antibody. In particular embodiments, the reference antibody is an IgG1, IgG2, or IgG3 antibody.

In certain embodiments, the reference antibody is abciximab, adalimumab, alemtuzumab, basiliximab, bevacizumab, cetuximab, certolizumab, daclizumab, eculizumab, efalizumab, gemtuzumab, ibritumomab, infliximab, muromonab, natalizumab, omalizumab, palivizumab, panitumumab, ranibizumab, rituximab, tositumomab, or trastuzumab.

In yet other embodiments, the reference glycoprotein is conjugated to a heterologous moiety. In some embodiments, the heterologous moiety is a polypeptide, nucleic acid, or small molecule. In particular embodiments, the reference glycoprotein is alefacept, abatacept, etanercept, rilonacept, or denileukin diftitox.

In some embodiments, the modified glycoprotein comprises two Fc regions, wherein one of the Fc regions comprises one or more amino acid substitutions, e.g., one or more amino acid substitutions described herein. In other embodiments, the modified glycoprotein comprises two Fc regions, wherein both Fc regions comprise one or more amino acid substitutions, e.g., one or more amino acid substitutions described herein.

In another aspect, the invention features a method of producing a modified glycoprotein. The method comprises expressing in a cell a recombinant modified glycoprotein comprising a modified amino acid sequence of a reference glycoprotein, wherein the reference glycoprotein comprises an immunoglobulin Fc region, or Fc fragment, wherein the modified glycoprotein comprises one or more amino acid substitutions of the Fc region, or Fc fragment, of the reference glycoprotein; and purifying the modified glycoprotein, wherein at least one of the amino acids substituted is F241, F243, K246, T260, or R301 of an IgG heavy chain.

In some embodiments, the cell is genetically engineered to express one or more exogenous glycosylation enzymes, e.g., one or more glycosyltransferase, e.g., one or more glycosyltransferase described herein. In other embodiments, the cell is genetically engineered to over-express or under-express an endogenous glycosylation enzyme, e.g., one or more endogenous glycosyltransferases, e.g., one or more endogenous glycosyltransferases described herein.

In some embodiments, at least one of the amino acid substitutions is F241A, F243A, K246A, T260A, or R301A.

In some embodiments, at least two of the amino acid substitutions are selected from F241A, F243A, K246A, T260A, and R301A. In particular embodiments, at least two of the amino acid substitutions are F241A and F243A; F241A and K246A; F241A and T260A; F241A and R301A; F243A and K246A; F243A and T260A; F243A and R301A; K246A and T260A; K246A and R301A; or T260A and R301A.

In some embodiments, the reference glycoprotein comprises a reference glycan, and the modified glycoprotein comprises a modified glycan having an altered composition relative to the reference glycan. In some embodiments, the modified glycan has an altered (e.g., increased or decreased) level of sialylation (e.g., alpha-2,6 or alpha-2,3 linked sialylation) relative to the reference glycan. In some embodiments, the modified glycan has an altered (e.g., increased or decreased) level of fucosylation (e.g., antennary fucosylation) relative to the reference glycan. In some embodiments, the modified glycan has an altered (e.g., increased or decreased) level of bisecting N-acetylglucosamine relative to the reference glycan.

In the level of sialylation, fucosylation, and/or bisecting N-acetylglucosamine in the modified glycan is increased by about 10%, about 20%, about 30%, about 40%, about 50%, about 60%, about 70%, about 80%, about 90%, about 100%, about 125%, about 150%, about 175%, about 200%, about 300%, about 400%, about 500%, or more, relative to the level in the reference glycan.

In other embodiments, the level of sialylation, fucosylation, and/or bisecting N-acetylglucosamine in the modified glycan is decreased by about 10%, about 20%, about 30%, about 40%, about 50%, about 60%, about 70%, about 80%, about 90%, about 100%, about 125%, about 150%, about 175%, about 200%, about 300%, about 400%, about 500%, or more, relative to the level in the reference glycan.

In some embodiments, the two or more amino acid substitutions result in increased sulfation of the modified glycan relative to the reference glycan.

In some embodiments, the modified glycoprotein has an altered activity (e.g., an altered activity described herein) relative to the reference glycoprotein. In some embodiments, the modified glycoprotein has a different, e.g., a detectably higher or lower, activity, such as an immune cell activating activity, e.g., Fc receptor affinity, Fc receptor specificity, complement activation activity, signaling activity, targeting activity, effector function, half-life, clearance, pro-inflammatory, anti-inflammatory, or transcytosis activity than a corresponding glycoprotein without the substituted amino acids. In some embodiments, the effector function is antibody dependent cellular cytotoxicity, complement dependent cytotoxicity, programmed cell death, or cellular phagocytosis.

In certain embodiments, the Fc receptor is an FcγRI, FcγRIIA, FcγRIIB, FcγRIIIA, FcγRIIIB FcγRIV, or FcRn receptor. In particular embodiments, the glycoprotein binds to an immune cell, e.g., a macrophage, neutrophil, dendritic cell, B cell, natural killer cell (NKC), or eosinophil.

In some embodiments, the reference glycoprotein is a reference antibody. In certain embodiments, the reference antibody is an IgA, IgD, IgE, IgG, or IgM antibody. In particular embodiments, the reference antibody is an IgG1, IgG2, or IgG3 antibody.

In certain embodiments, the reference antibody is abciximab, adalimumab, alemtuzumab, basiliximab, bevacizumab, cetuximab, certolizumab, daclizumab, eculizumab, efalizumab, gemtuzumab, ibritumomab, infliximab, muromonab, natalizumab, omalizumab, palivizumab, panitumumab, ranibizumab, rituximab, tositumomab, or trastuzumab.

In yet other embodiments, the reference glycoprotein is conjugated to a heterologous moiety. In some embodiments, the heterologous moiety is a polypeptide, nucleic acid, or small molecule. In particular embodiments, the reference glycoprotein is alefacept, abatacept, etanercept, rilonacept, or denileukin diftitox.

In some embodiments, the modified glycoprotein comprises two Fc regions, wherein one of the Fc regions comprises one or more amino acid substitutions, e.g., one or more amino acid substitutions described herein. In other embodiments, the modified glycoprotein comprises two Fc regions, wherein both Fc regions comprise one or more amino acid substitutions, e.g., one or more amino acid substitutions described herein.

In another aspect, the invention features a method of producing a modified glycoprotein. The method comprises providing a nucleotide sequence encoding a reference glycoprotein comprising an immunoglobulin Fc region, or Fc fragment; modifying the nucleotide sequence to encode a modified Fc region or Fc fragment comprising one or more amino acid substitutions relative to the reference glycoprotein; and expressing the modified glycoprotein encoded by the modified nucleotide sequence in a cell, thereby producing the modified glycoprotein.

In some embodiments, the cell is genetically engineered to express one or more exogenous glycosylation enzymes, e.g., one or more glycosyltransferase, e.g., one or more glycosyltransferase described herein. In other embodiments, the cell is genetically engineered to over-express or under-express an endogenous glycosylation enzyme, e.g., one or more endogenous glycosyltransferases, e.g., one or more endogenous glycosyltransferases described herein.

In some embodiments, at least one of the amino acids substituted is F241, F243, K246, T260, or R301 of an IgG heavy chain. In some embodiments, at least one of the amino acid substitutions is F241A, F243A, K246A, T260A, or R301A.

In some embodiments, the modified glycoprotein comprises two or more amino acid substitutions of the Fc region, or Fc fragment, of the reference glycoprotein. In some embodiments, at least two of the amino acid substitutions are selected from F241A, F243A, K246A, T260A, and R301A. In particular embodiments, at least two of the amino acid substitutions are F241A and F243A; F241A and K246A; F241A and T260A; F241A and R301A; F243A and K246A; F243A and T260A; F243A and R301A; K246A and T260A; K246A and R301A; or T260A and R301A.

In some embodiments, the reference glycoprotein comprises a reference glycan, and the modified glycoprotein comprises a modified glycan having an altered composition relative to the reference glycan. In some embodiments, the modified glycan has an altered (e.g., increased or decreased) level of sialylation (e.g., alpha-2,6 or alpha-2,3 linked sialylation) relative to the reference glycan. In some embodiments, the modified glycan has an altered (e.g., increased or decreased) level of fucosylation (e.g., antennary fucosylation) relative to the reference glycan. In some embodiments, the modified glycan has an altered (e.g., increased or decreased) level of bisecting N-acetylglucosamine relative to the reference glycan.

In some embodiments, the level of sialylation, fucosylation, and/or bisecting N-acetylglucosamine in the modified glycan is increased by about 10%, about 20%, about 30%, about 40%, about 50%, about 60%, about 70%, about 80%, about 90%, about 100%, about 125%, about 150%, about 175%, about 200%, about 300%, about 400%, about 500%, or more, relative to the level in the reference glycan.

In other embodiments, the level of sialylation, fucosylation, and/or bisecting N-acetylglucosamine in the modified glycan is decreased by about 10%, about 20%, about 30%, about 40%, about 50%, about 60%, about 70%, about 80%, about 90%, about 100%, about 125%, about 150%, about 175%, about 200%, about 300%, about 400%, about 500%, or more, relative to the level in the reference glycan.

In some embodiments, the one or more amino acid substitutions result in increased sulfation of the modified glycan relative to the reference glycan.

In some embodiments, the modified glycoprotein has an altered activity (e.g., an altered activity described herein) relative to the reference glycoprotein. In some embodiments, the modified glycoprotein has a different, e.g., a detectably higher or lower, activity, such as an immune cell activating activity, e.g., Fc receptor affinity, Fc receptor specificity, complement activation activity, signaling activity, targeting activity, effector function, half-life, clearance, pro-inflammatory, anti-inflammatory, or transcytosis activity than a corresponding glycoprotein without the substituted amino acids. In some embodiments, the effector function is antibody dependent cellular cytotoxicity, complement dependent cytotoxicity, programmed cell death, or cellular phagocytosis.

In certain embodiments, the Fc receptor is an FcγRI, FcγRIIA, FcγRIIB, FcγRIIIA, FcγRIIIB FcγRIV, or FcRn receptor. In particular embodiments, the glycoprotein binds to an immune cell, e.g., a macrophage, neutrophil, dendritic cell, B cell, natural killer cell (NKC), or eosinophil.

In some embodiments, the reference glycoprotein is a reference antibody. In certain embodiments, the reference antibody is an IgA, IgD, IgE, IgG, or IgM antibody. In particular embodiments, the reference antibody is an IgG1, IgG2, or IgG3 antibody.

In certain embodiments, the reference antibody is abciximab, adalimumab, alemtuzumab, basiliximab, bevacizumab, cetuximab, certolizumab, daclizumab, eculizumab, efalizumab, gemtuzumab, ibritumomab, infliximab, muromonab, natalizumab, omalizumab, palivizumab, panitumumab, ranibizumab, rituximab, tositumomab, or trastuzumab.

In yet other embodiments, the reference glycoprotein is conjugated to a heterologous moiety. In some embodiments, the heterologous moiety is a polypeptide, nucleic acid, or small molecule. In particular embodiments, the reference glycoprotein is alefacept, abatacept, etanercept, rilonacept, or denileukin diftitox.

In some embodiments, the modified glycoprotein comprises two Fc regions, wherein one of the Fc regions comprises one or more amino acid substitutions, e.g., one or more amino acid substitutions described herein. In other embodiments, the modified glycoprotein comprises two Fc regions, wherein both Fc regions comprise one or more amino acid substitutions, e.g., one or more amino acid substitutions described herein.

In another aspect, the invention features a modified glycoprotein produced by any of the methods described herein.

In another aspect, the invention features a method of treating a subject with a therapeutic glycoprotein. The method comprises administering a modified glycoprotein described herein to a subject in need thereof, thereby treating the subject.

In some embodiments, the subject is a mammal, e.g., a human or non-human primate (such as an ape, monkey, orangutan, or chimpanzee), a dog, cat, guinea pig, rabbit, rat, mouse, horse, cattle, or cow.

BRIEF DESCRIPTION OF THE DRAWINGS

The present teachings described herein will be more fully understood from the following description of various illustrative embodiments, when read together with the accompanying drawings. It should be understood that the drawings described below are for illustration purposes only and are not intended to limit the scope of the present teachings in any way.

FIG. 2A is the amino acid sequence of the heavy chain of wild type rituximab. FIG. 2B is the amino acid sequence of mutant 1 (F241A, F243A) of the heavy chain of rituximab (SEQ ID NO: 2). FIG. 2C is the amino acid sequence of mutant 2 (F243A, R301A) of the heavy chain of rituximab (SEQ ID NO: 3). FIG. 2D is the amino acid sequence of mutant 3 (K246A, T260A) of the heavy chain of rituximab (SEQ ID NO: 4). FIG. 2E is the amino acid sequence of mutant 4 (T260A, R301A) of the heavy chain of rituximab (SEQ ID NO: 5).

DETAILED DESCRIPTION

Figure 1:
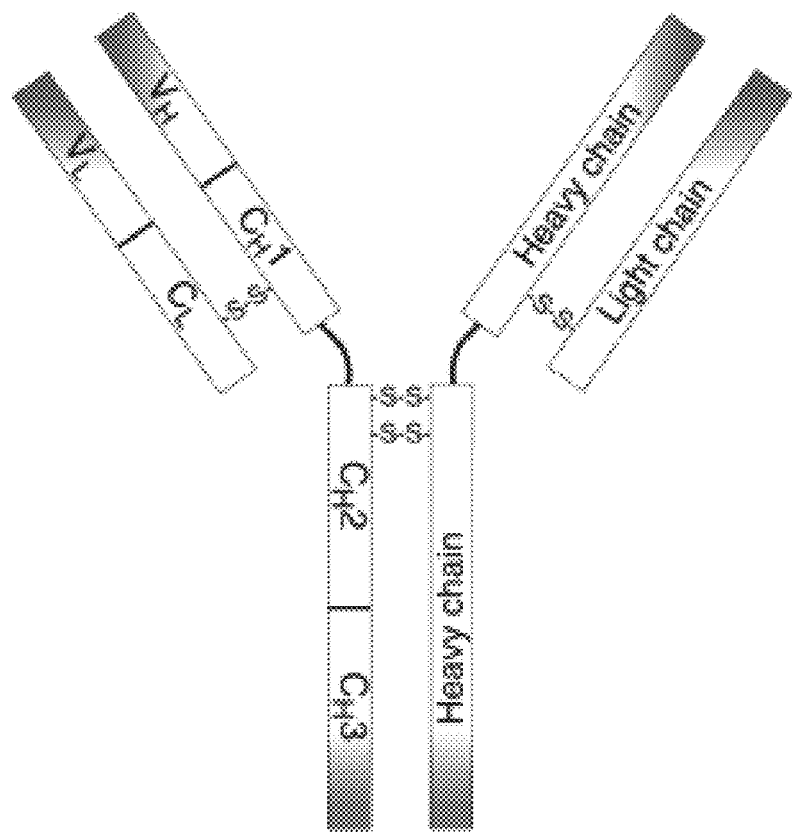
FIG. 1 is a schematic illustration of an IgG antibody molecule.

The constant regions (Fc regions) of antibodies interact with cellular binding partners to mediate antibody function and activity, such as antibody-dependent effector functions and complement activation. For IgG type antibodies, the binding sites for complement C1q and Fc receptors (FcγRs) are located in the CH2 domain of the Fc region.

The coexpression of activating and inhibitory FcRs on different target cells modulates antibody-mediated immune responses. In addition to their involvement in the efferent phase of an immune response, FcRs are also important for regulating B cell and dendritic cell (DC) activation. For example, in the case of IgG type antibodies, different classes of FcγR mediate various cellular responses, such as phagocytosis by macrophages, antibody-dependent cell-mediated cytotoxicity by NK cells, and degranulation of mast cells. Each FcγR displays different binding affinities and IgG subclass specificities. Lectin receptors also play a role. For example, Dc-SIGN has been shown to play a role in the anti-inflammatory activity of Fc, e.g., in IVIG (see, e.g., WO2008057634; WO2009132130).

Antibodies are glycosylated at conserved positions in the constant regions of their heavy chain. For example, IgG antibodies have a single N-linked glycosylation site at Asn297 of the CH2 domain. Each antibody isotype has a distinct variety of N-linked carbohydrate structures in the constant regions. For human IgG, the core oligosaccharide normally consists of GlcNAc$_2$Man$_3$GlcNAc, with differing numbers of outer residues. Variation among individual IgG's can occur via attachment of galactose and/or galactose-sialic acid at the two terminal GlcNAc or via attachment of a third GlcNAc arm (bisecting GlcNAc).

The present disclosure provides compositions and methods for manipulating the biological activity of an Fc domain-containing glycoprotein (e.g., an immunoglobulin) by modifying the amino acid sequence of the Fc domain, thereby allowing altered glycosylation of the Fc domain, e.g., within a host cell, within an engineered host cell (e.g., a host cell engineered to express an exogenous glycosylation enzyme or to over-express or under-express an endogenous glycosylation enzyme), or on a purified Fc-containing glycoprotein. While not bound by theory, it is posited that by altering certain amino acids of the Fc domain, the ability of the Fc glycosylation sites to be accessed and altered by glycosyltransferases and other glycosylation enzymes was improved (e.g., during expression in a host cell and/or in-vitro post production), thereby resulting in an Fc domain-containing protein with altered glycosylation and altered or improved biological or therapeutic function.

For example, the present disclosure provides that the biological activity of an immunoglobulin can be manipulated, altered, or controlled by increasing Fc sulfation and that Fc sulfation can be increased by altering certain amino acids of the Fc region (e.g., by increasing sulfation post-production as disclosed herein). Biological activities that can be manipulated, altered, or controlled in light of the present disclosure include, for example, one or more of: Fc receptor binding, Fc receptor affinity, Fc receptor specificity, complement activation, signaling activity, targeting activity, effector function (such as programmed cell death or cellular phagocytosis), half-life, clearance, and transcytosis. Described herein are glycoproteins (e.g., IVIG, antibodies or fusion proteins, such as Fc fusion proteins) that include a modified (e.g., mutated) constant region of an immunoglobulin, and have altered glycosylation and/or an altered activity and/or function relative to the unmodified glycoprotein. Methods of making and using such compositions are also described.

Definitions

As used herein, "glycan" is a sugar, which can be monomers or polymers of sugar residues, such as at least three sugars, and can be linear or branched. A "glycan" can include natural sugar residues (e.g., glucose, N-acetylglucosamine, N-acetyl neuraminic acid, galactose, mannose, fucose, hexose, arabinose, ribose, xylose, etc.) and/or modified sugars (e.g., 2'-fluororibose, 2'-deoxyribose, phosphomannose, 6'sulfo N-acetylglucosamine, etc.). The term "glycan" includes homo and heteropolymers of sugar residues. The term "glycan" also encompasses a glycan component of a glycoconjugate (e.g., of a glycoprotein, glycolipid, proteoglycan, etc.). The term also encompasses free glycans, including glycans that have been cleaved or otherwise released from a glycoconjugate.

As used herein, the term "glycoprotein" refers to a protein that contains a peptide backbone covalently linked to one or more sugar moieties (i.e., glycans). The sugar moiety(ies) may be in the form of monosaccharides, disaccharides, oligosaccharides, and/or polysaccharides. The sugar moiety (ies) may comprise a single unbranched chain of sugar residues or may comprise one or more branched chains. Glycoproteins can contain O-linked sugar moieties and/or N-linked sugar moieties.

By "purified" (or "isolated") refers to a nucleic acid sequence (e.g., a polynucleotide) or an amino acid sequence (e.g., a polypeptide) that is removed or separated from other components present in its natural environment. For example, an isolated polypeptide is one that is separated from other components of a cell in which it was produced (e.g., the endoplasmic reticulum or cytoplasmic proteins and RNA). An isolated polynucleotide is one that is separated from other nuclear components (e.g., histones) and/or from upstream or downstream nucleic acid sequences. An isolated nucleic acid sequence or amino acid sequence can be at least 60% free, or at least 75% free, or at least 90% free, or at least 95% free from other components present in natural environment of the indicated nucleic acid sequence or amino acid sequence.

As used herein, "polynucleotide" (or "nucleotide sequence" or "nucleic acid molecule") refers to an oligonucleotide, nucleotide, or polynucleotide, and fragments or portions thereof, and to DNA or RNA of genomic or synthetic origin, which may be single- or double-stranded, and represent the sense or anti-sense strand.

As used herein, "polypeptide" (or "amino acid sequence" or "protein") refers to an oligopeptide, peptide, polypeptide, or protein sequence, and fragments or portions thereof, and to naturally occurring or synthetic molecules. "Amino acid sequence" and like terms, such as "polypeptide" or "protein", are not meant to limit the indicated amino acid sequence to the complete, native amino acid sequence associated with the recited protein molecule.

The articles "a" and "an" are used herein to refer to one or to more than one (i.e., to at least one) of the grammatical object of the article. By way of example, "an element" means one element or more than one element.

The term "about" is used herein to mean a value – or +20% of a given numerical value. Thus, "about 60%" means a value of between 60-(20% of 60) and 60+(20% of 60) (i.e., between 48 and 70).

The term "pharmaceutically effective amount" or "therapeutically effective amount" refers to an amount (e.g., dose) effective in treating a patient, having a disorder or condition described herein. It is also to be understood herein that a "pharmaceutically effective amount" may be interpreted as an amount giving a desired therapeutic effect, either taken in one dose or in any dosage or route, taken alone or in combination with other therapeutic agents.

The term "treatment" or "treating", as used herein, refers to administering a therapy in an amount, manner, and/or mode effective to improve a condition, symptom, or parameter associated with a disorder or condition or to prevent or reduce progression of a disorder or condition, to a degree detectable to one skilled in the art. An effective amount, manner, or mode can vary depending on the subject and may be tailored to the subject.

The term "subject", as used herein, means any subject for whom diagnosis, prognosis, or therapy is desired. For example, a subject can be a mammal, e.g., a human or non-human primate (such as an ape, monkey, orangutan, or chimpanzee), a dog, cat, guinea pig, rabbit, rat, mouse, horse, cattle, or cow.

As used herein, the term "antibody" refers to a polypeptide that includes at least one immunoglobulin variable region, e.g., an amino acid sequence that provides an immunoglobulin variable domain or immunoglobulin variable domain sequence. For example, an antibody can include a heavy (H) chain variable region (abbreviated herein as VH), and a light (L) chain variable region (abbreviated herein as VL). In another example, an antibody includes two heavy (H) chain variable regions and two light (L) chain variable regions. The term "antibody" encompasses antigen-binding fragments of antibodies (e.g., single chain antibodies, Fab, F(ab')$_2$, Fd, Fv, and dAb fragments) as well as complete antibodies, e.g., intact immunoglobulins of types IgA, IgG, IgE, IgD, IgM (as well as subtypes thereof). The light chains of the immunoglobulin can be of types kappa or lambda.

As used herein, the term "constant region" refers to a polypeptide that corresponds to, or is derived from, one or more constant region immunoglobulin domains of an antibody. A constant region can include any or all of the following immunoglobulin domains: a CHI domain, a hinge region, a CH2 domain, a CH3 domain (derived from an IgA, IgD, IgG, IgE, or IgM), and a CH4 domain (derived from an IgE or IgM).

As used herein, the term "Fc region" refers to a dimer of two "Fc polypeptides", each "Fc polypeptide" comprising the constant region of an antibody excluding the first constant region immunoglobulin domain. In some embodiments, an "Fc region" includes two Fc polypeptides linked by one or more disulfide bonds, chemical linkers, or peptide linkers. "Fc polypeptide" refers to the last two constant region immunoglobulin domains of IgA, IgD, and IgG, and the last three constant region immunoglobulin domains of IgE and IgM, and may also include part or all of the flexible hinge N-terminal to these domains. For IgG, "Fc polypeptide" comprises immunoglobulin domains Cgamma2 (Cγ2) and Cgamma3 (Cγ3) and the lower part of the hinge between Cgamma1 (Cγ1) and Cγ2. Although the boundaries of the Fc polypeptide may vary, the human IgG heavy chain Fc polypeptide is usually defined to comprise residues starting at T223 or C226 or P230, to its carboxyl-terminus, wherein the numbering is according to the EU index as in Kabat et al. (1991, NIH Publication 91-3242, National Technical Information Services, Springfield, Va.). For IgA, Fc polypeptide comprises immunoglobulin domains Calpha2 (Cα2) and Calpha3 (Cα3) and the lower part of the hinge between Calpha1 (Cα1) and Cα2. An Fc region can be synthetic, recombinant, or generated from natural sources such as IVIG.

As used herein, the term "Fc region variant" refers to an analog of an Fc region that possesses one or more Fc-mediated activities described herein. This term includes Fc regions comprising one or more amino acid modifications (e.g., substitutions, additions, or deletions) relative to a wild type or naturally existing Fc region. For example, variant Fc regions can possess at least about 50% homology, at least about 75% homology, at least about 80% homology, at least about 85%, homology, at least about 90% homology, at least about 95% homology, or more, with a naturally existing Fc region. Fc region variants also include Fc regions comprising one or more amino acid residues added to or deleted from the N- or C-terminus of a wild type Fc region.

As used herein, an "N-glycosylation site of an Fc region" refers to an amino acid residue within an Fc region to which a glycan is N-linked.

As used herein, the terms "coupled", "linked", "joined", "fused", and "fusion" are used interchangeably. These terms refer to the joining together of two more elements or components by whatever means, including chemical conjugation or recombinant means.

The terms "overexpress," "overexpression" or "overexpressed" interchangeably refer to a protein or nucleic acid that is transcribed or translated at a detectably greater level, such as in a cancer cell, in comparison to a control cell. The term includes expression due to transcription, post transcriptional processing, translation, post-translational processing, cellular localization (e.g., organelle, cytoplasm, nucleus, cell surface), and RNA and protein stability, as compared to a control cell. Overexpression can be detected using conventional techniques, e.g., for detecting mRNA (i.e., RT-PCR, PCR, hybridization) or proteins (i.e., ELISA, immunohistochemical techniques). Overexpression can be expression in an amount greater than about 10%, 20%, 30%, 40%, 50%, 60%, 70%, 80%, 90% or more compared to a control cell. In certain instances, overexpression is 1-fold, 2-fold, 3-fold, 4-fold, or more, higher level of transcription or translation compared to a control cell.

I. Glycoproteins

As described herein, one or more amino acid residues of Fc regions of antibodies have been mutated to modify glycan composition relative to a corresponding wild type antibody, affecting specific binding to Fc receptors and antibody effector function. Accordingly, glycoproteins are described herein that include an immunoglobulin Fc region, wherein the Fc region contains one, two, or more amino acid modifications (e.g., substitutions) of a corresponding wild type glycoprotein. In one instance, a glycoprotein that includes an Fc region (e.g., a glycoprotein that includes a CH2 domain of an Fc region of an antibody heavy chain) can be mutated using methods disclosed herein to modify antibody-mediated functions, such as Fc-mediated effector functions. Further, the particular modification (i.e., increased or decreased effector function) can be controlled by introducing specific amino acid mutations into the Fc region. Such methods can be used, for example, to modulate the activity, such as the therapeutic activity, of a glycoprotein.

Glycoproteins include, for example, any of a variety of hematologic agents (including, for instance, erythropoietin, blood-clotting factors, etc.), interferons, colony stimulating factors, antibodies, enzymes, and hormones. The identity of a particular glycoprotein is not intended to limit the present disclosure, and any glycoprotein of interest can be sulfated using the present methods.

In addition to an Fc region or fragment thereof having one or more modified amino acid residues, a glycoprotein described herein can also include a target-binding domain that binds to a target of interest (e.g., binds to an antigen). For example, a glycoprotein, such as an antibody, can bind to a transmembrane polypeptide (e.g., receptor) or ligand (e.g., a growth factor). Exemplary molecular targets (e.g., antigens) for glycoproteins described herein (e.g., antibodies) include CD proteins such as CD2, CD3, CD4, CD8, CD11, CD19, CD20, CD22, CD25, CD33, CD34, CD40, CD52; members of the ErbB receptor family such as the EGF receptor (EGFR, HER1, ErbB1), HER2 (ErbB2), HER3 (ErbB3) or HER4 (ErbB4) receptor; macrophage receptors such as CRIg; tumor necrosis factors such as TNFα or TRAIL/Apo-2; cell adhesion molecules such as LFA-1, Mac1, p150,95, VLA-4, 1CAM-1, VCAM and αvβ3 integrin including either α or β subunits thereof (e.g., anti-CD11a, anti-CD 18 or anti-CD11b antibodies); growth factors and receptors such as EGF, FGFR (e.g., FGFR3) and VEGF; IgE; cytokines such as IL1; cytokine receptors such as IL2 receptor; blood group antigens; flk2/flt3 receptor; obesity (OB) receptor; mpl receptor; CTLA-4; protein C; neutropilins; ephrins and receptors; netrins and receptors; slit and receptors; chemokines and chemookine receptors such as CCL5, CCR4, CCR5; amyloid beta; complement factors, such as complement factor D; lipoproteins, such as oxidized LDL (oxLDL); lymphotoxins, such as lymphotoxin alpha (LTa). Other molecular targets include Tweak, B7RP-1, proprotein convertase subtilisin/kexin type 9 (PCSK9), sclerostin, c-kit, Tie-2, c-fms, and anti-M1.

Nonlimiting, exemplary reference glycoproteins (e.g., that can be modified by one or more amino acids as described herein) that include an Fc region of an antibody heavy chain include abatacept (Orencia®, Bristol-Myers Squibb), abciximab (ReoPro®, Roche), adalimumab (Humira®, Bristol-Myers Squibb), alefacept (Amevive®, Astellas Pharma), alemtuzumab (Campath®, Genzyme/Bayer), basiliximab (Simulect®, Novartis), bevacizumab (Avastin®, Roche), certolizumab (CIMZIA®, UCB, Brussels, Belgium), cetuximab (Erbitux®, Merck-Serono), daclizumab (Zenapax®, Hoffmann-La Roche), denileukin diftitox (Ontak®, Eisai), eculizumab (Soliris®, Alexion Pharmaceuticals), efalizumab (Raptiva®, Genentech), etanercept (Enbrel®, Amgen-Pfizer), gemtuzumab (Mylotarg®, Pfizer), ibritumomab (Zevalin®, Spectrum Pharmaceuticals), infliximab (Remicade®, Centocor), muromonab (Orthoclone OKT3®, Janssen-Cilag), natalizumab (Tysabri®, Biogen Idec, Elan), omalizumab (Xolair®, Novartis), palivizumab (Synagis®, MedImmune), panitumumab (Vectibix®, Amgen), ranibizumab (Lucentis®, Genentech), rilonacept (Arcalyst®, Regeneron Pharmaceuticals), rituximab (MabThera®, Roche), tositumomab (Bexxar®, GlaxoSmithKline), and trastuzumab (Herceptin®, Roche).

A. N-Linked Glycosylation

N-linked oligosaccharide chains are added to a protein in the lumen of the endoplasmic reticulum (see *Molecular Biology of the Cell*, Garland Publishing, Inc. (Alberts et al., 1994)). Specifically, an initial oligosaccharide (typically 14-sugar) is added to the amino group on the side chain of an asparagine residue contained within the target consensus sequence of Asn-X-Ser/Thr, where X may be any amino acid except praline. The structure of this initial oligosaccharide is common to most eukaryotes, and contains 3 glucose, 9 mannose, and 2 N-acetylglucosamine residues. This initial oligosaccharide chain can be trimmed by specific glycosidase enzymes in the endoplasmic reticulum, resulting in a short, branched core oligosaccharide composed of two N-acetylglucosamine and three mannose residues.

N-glycans can be subdivided into three distinct groups called "high mannose type", "hybrid type", and "complex type", with a common pentasaccharide core (Man (alpha1, 6)-(Man(alpha1,3))-Man(beta1,4)-GlcpNAc(beta 1,4)-GlcpNAc(beta 1,N)-Asn) occurring in all three groups.

After initial processing in the endoplasmic reticulum, the glycoprotein is transported to the Golgi where further processing may take place. If the glycan is transferred to the Golgi before it is completely trimmed to the core pentasaccharide structure, it results in a "high-mannose glycan".

Additionally or alternatively, one or more monosaccharides units of N-acetylglucosamine may be added to the core mannose subunits to form a "complex glycan". Galactose may be added to the N-acetylglucosamine subunits, and sialic acid subunits may be added to the galactose subunits, resulting in chains that terminate with any of a sialic acid, a galactose or an N-acetylglucosamine residue. Additionally, a fucose residue may be added to an N-acetylglucosamine residue of the core oligosaccharide. Each of these additions is catalyzed by specific glycosyl transferases, known in the art.

"Hybrid glycans" comprise characteristics of both high-mannose and complex glycans. For example, one branch of a hybrid glycan may comprise primarily or exclusively mannose residues, while another branch may comprise N-acetylglucosamine, sialic acid, galactose, and/or fucose sugars.

N-linked Glycosylation in Antibodies

Antibodies are glycosylated at conserved, N-linked glycosylation sites in the constant region of immunoglobulin heavy chains. For example, IgG antibodies have a single N-linked glycosylation site at Asn297 of the CH2 domain (see Jefferis, Nature Reviews 8:226-234 (2009)). IgA antibodies have N-linked glycosylation sites within the CH2 and CH3 domains, IgE antibodies have N-linked glycosylation sites within the CH3 domain, and IgM antibodies have N-linked glycosylation sites within the CH1, CH2, CH3, and CH4 domains (see Arnold et al., J. Biol. Chem. 280:29080-29087 (2005); Mattu et al., J. Biol. Chem. 273:2260-2272 (1998); Nettleton et al., Int. Arch. Allergy Immunol. 107: 328-329 (1995)).

Each antibody isotype has a distinct variety of N-linked carbohydrate structures in the constant regions. For example, IgG has a single N-linked biantennary carbohydrate at Asn297 of the CH2 domain in the Fc region, which also contains the binding sites for C1q and FcγR (see Jefferis et al., Immunol. Rev. 163:59-76 (1998); and Wright et al., Trends Biotech 15:26-32 (1997)). For human IgG, the core oligosaccharide normally consists of GlcNAc2Man3GlcNAc, with differing numbers of outer residues. Variation among individual IgG can occur via attachment of galactose and/or galactose-sialic acid at the two terminal GlcNAc or via attachment of a third GlcNAc arm (bisecting GlcNAc). Although accounting for only 23% of antibody mass, glycosylation of the IgG-Fc has been shown to be important for effector functions.

B. Antibodies

The basic structure of an IgG antibody is illustrated in FIG. 1. As shown in FIG. 1, an IgG antibody consists of two identical light polypeptide chains and two identical heavy polypeptide chains linked together by disulphide bonds. The first domain located at the amino terminus of each chain is variable in amino acid sequence, providing the antibody binding specificities found in each individual antibody. These are known as variable heavy (VH) and variable light (VL) regions. The other domains of each chain are relatively invariant in amino acid sequence and are known as constant heavy (CH) and constant light (CL) regions. As shown in FIG. 1, for an IgG antibody, the light chain includes one variable region (VL) and one constant region (CL). An IgG heavy chain includes a variable region (VH), a first constant region (CH1), a hinge region, a second constant region (CH2), and a third constant region (CH3). In IgE and IgM antibodies, the heavy chain includes an additional constant region (CH4).

Antibodies described herein can include, for example, monoclonal antibodies, polyclonal antibodies, multispecific antibodies, human antibodies, humanized antibodies, camelized antibodies, chimeric antibodies, single-chain Fvs (scFv), disulfide-linked Fvs (sdFv), and anti-idiotypic (anti-Id) antibodies, and antigen-binding fragments of any of the above. Antibodies can be of any type (e.g., IgG, IgE, IgM, IgD, IgA and IgY), class (e.g., IgG1, IgG2, IgG3, IgG4, IgA1 and IgA2) or subclass.

The term "Fc fragment", as used herein, refers to one or more fragments of an Fc region that retains an Fc function and/or activity described herein, such as binding to an Fc receptor. Examples of such fragments include fragments that include an N-linked glycosylation site of an Fc region (e.g., an Asn297 of an IgG heavy chain or homologous sites of other antibody isotypes), such as a CH2 domain. The term "antigen binding fragment" of an antibody, as used herein, refers to one or more fragments of an antibody that retain the ability to specifically bind to an antigen. Examples of binding fragments encompassed within the term "antigen binding fragment" of an antibody include a Fab fragment, a F(ab')2 fragment, a Fd fragment, a Fv fragment, a scFv fragment, a dAb fragment (Ward et al., (1989) Nature 341:544-546), and an isolated complementarity determining region (CDR). These antibody fragments can be obtained using conventional techniques known to those with skill in the art, and the fragments can be screened for utility in the same manner as are intact antibodies.

Antibodies or fragments (e.g., reference antibodies or fragments of the compositions and methods described herein) can be produced by any method known in the art for the synthesis of antibodies (sec, e.g., Harlow et al., Antibodies: A Laboratory Manual, (Cold Spring Harbor Laboratory Press, 2nd ed. 1988); Brinkman et al., 1995, J. Immunol. Methods 182:41-50; WO 92/22324; WO 98/46645). Chimeric antibodies can be produced using the methods described in, e.g., Morrison, 1985, Science 229: 1202, and humanized antibodies by methods described in, e.g., U.S. Pat. No. 6,180,370.

Additional antibodies of the compositions and methods described herein are bispecific antibodies and multivalent antibodies, as described in, e.g., Segal et al., J. Immunol. Methods 248:1-6 (2001); and Tutt et al., J. Immunol. 147: 60 (1991).

C. Amino Acid Modifications of the Fc Region

The amino acid sequence of a glycoprotein described herein can be modified to produce an Fc region variant, such as an Fc region having at least one (e.g., 1, 2, 3, 4, 5, 6, 7, 8, 9, 10, or more) addition, substitution, or deletion of a wild-type amino acid residue. The amino acid residue(s) to be modified can be one or more amino acid residue(s) involved in or proximate to an interaction of an Fc region and a glycan, and/or involved in an effector function described herein. For example, the crystal structures for Fc dimers with glycans bound to FcγRIII are known (see, e.g., Mizushima et al., Genes to Cells 16:1071-1080 (2011); Ferrara et al., PNAS 108: 12669-12674 (2011)). Accordingly, one or more of the amino acids of the Fc region near or proximal to a bound glycan (e.g., an Fc region amino acid putatively involved in hydrogen bonding and/or Van Der Waals forces with a glycan) can be modified.

Specific, nonlimiting amino acid residues that can be modified include, e.g., F241, F243, K246, T260, Y296, S298, and R301 (Kabat numbering) of an IgG1 immunoglobulin heavy chain, or the corresponding amino acid residues of other immunoglobulins. These amino acid residues can be substituted with any amino acid or amino acid analog. For example, the substitutions at the recited positions can be made with any of the naturally-occurring amino acids (e.g., alanine, aspartic acid, asparagine, arginine, cysteine, glycine, glutamic acid, glutamine, histidine, leucine, valine, isoleucine, lysine, methionine, proline, threonine, serine, phenylalanine, tryptophan, or tyrosine). In particular instances, an amino acid residue is substituted with alanine.

The glycoproteins described herein can include additional modifications of the Fc region. For example, the binding site on human and murine antibodies for FcγR have been mapped to the "lower hinge region" consisting of residues 233-239 (EU index numbering as in Kabat et al., Sequences of Proteins of Immunological Interest, 5th Ed. Public Health Service, National Institutes of Health, Bethesda, Md. (1991); see Woof et al., Molec. Immunol. 23:319-330 (1986); Duncan et al., Nature 332:563 (1988)). Accordingly, an Fc region variant can include a modification of one or more of amino acids 233-239. Other amino acids that can be modified include G316-K338; K274-R301; and Y407-R416 (Shields et al., J. Biol. Chem. 9:6591-6604 (2001)).

Additionally, a number of different Fc region amino acids that may comprise the binding site for C1q have been identified. These include residues 231-238, 318, 320, 322, and 331 (Kabat numbering) (see, e.g., U.S. Pat. No. 6,194,551; WO 99/51642; Idusogie et al., J. Immunol. 164:4178-4184 (2000). Thus, an Fc region variant can include a modification of one or more of these amino acids (e.g., a modification of 1, 2, 3, 4, 5, 6, 7, 8, 9, 10, or more of these amino acids).

Glycoproteins having one or more amino acid residue modifications described herein can be produced according to molecular biology and recombinant gene expression methods known in the art and described herein.

D. Glycan Modifications

Glycoproteins modified by one or more amino acid residues described herein have modified glycan compositions relative to corresponding wild type or reference glycoproteins. For example, in the case of IgG antibodies, a mutated glycoprotein described herein can have altered (e.g., increased or decreased) levels of mannose, N-acetylglucosamine, sialic acid, galactose, and/or fucose sugars, relative to a corresponding wild type or reference IgG antibody. The altered levels can be measured on an individual glycan (e.g., an increase or decrease in the number or type of sugars on a particular glycan), or the overall composition of a preparation of glycoproteins can be modified (e.g., a higher or lower number or percentage of a preparation of modified glycoproteins can have a particular glycan composition relative to a corresponding wild type or reference glycoprotein).

In some embodiments, the glycoproteins modified by one or more amino acid residues described herein are transfected and expressed in a host cell, wherein the endogenous cellular glycosylation machinery of the host cell produces a glycoprotein having modified glycans relative to a corresponding wild type or reference glycoprotein expressed under the same conditions in the same host cell.

In other embodiments, the glycoproteins modified by one or more amino acid residues described herein are transfected and expressed in a host cell engineered to express one or more exogenous glycosylation enzymes, e.g., one or more glycosyltransferase, e.g., one or more glycosyltransfcrase described herein, wherein the cellular glycosylation machinery of the engineered host cell produces a glycoprotein having modified glycans relative to a corresponding wild type or reference glycoprotein expressed under the same conditions in the same engineered host cell.

In yet other embodiments, the glycoproteins modified by one or more amino acid residues described herein are transfected and expressed in a host cell engineered to over-express or under-express one or more endogenous glycosylation enzymes, e.g., one or more glycosyltransferase, e.g., one or more glycosyltransferase described herein, wherein the cellular glycosylation machinery of the engineered host cell produces a glycoprotein having modified glycans relative to a corresponding wild type or reference glycoprotein expressed under the same conditions in the same engineered host cell.

In other embodiments, the glycoproteins modified by one or more amino acid residues described herein are expressed in a host cell and purified from the host cell, and the purified glycoprotein is modified, e.g., enzymatically modified in-vitro with one or more glycosylation enzymes, e.g., one or more glycosyltransferases, e.g., one or more glycosyltransferases disclosed herein, to produce a glycoprotein having modified glycans relative to a corresponding wild type or reference glycoprotein expressed under the same conditions in the same host cell.

E. Glycoprotein Conjugates

The disclosure includes modified glycoproteins (or modified Fc regions or Fc fragments containing an N-glycosylation site thereof) that are conjugated or fused to one or more heterologous moieties. The modification of such glycoprotein conjugates modifies the glycan composition and one or more Fc-mediated functions described herein. Heterologous moieties include, but are not limited to, peptides, polypeptides, proteins, fusion proteins, nucleic acid molecules, small molecules, mimetic agents, synthetic drugs, inorganic molecules, and organic molecules. In some instances, the methods described herein modify a fusion protein that comprises a peptide, polypeptide, protein scaffold, scFv, dsFv, diabody, Tandab, or an antibody mimetic fused to an Fc region, such as a glycosylated Fc region. The fusion protein can include a linker region connecting the Fc region to the heterologous moiety (see, e.g., Hallewell et al. (1989), J. Biol. Chem. 264, 5260-5268; Alfthan et al. (1995), Protein Eng. 8, 725-731; Robinson & Sauer (1996)).

Exemplary, nonlimiting reference fusion proteins described herein include abatacept (Orencia®, Bristol-Myers Squibb), alefacept (Amevive®, Astellas Pharma), denileukin diftitox (OntafoID, Eisai), etanercept (Enbrel®, Amgen-Pfizer), and rilonacept (Arcalyst®, Regeneron Pharmaceuticals).

In some instances, a modified Fc region (or a modified Fc fragment containing an N-glycosylation site thereof) is conjugated to a heterologous polypeptide of at least 10, at least 20, at least 30, at least 40, at least 50, at least 60, at least 70, at least 80, at least 90 or at least 100 amino acids.

In some instances, a fusion protein can include a modified Fc region (or a modified Fc fragment containing an N-glycosylation site thereof) conjugated to marker sequences, such as a peptide to facilitate purification. A particular marker amino acid sequence is a hexa-histidine peptide, such as the tag provided in a pQE vector (QIAGEN, Inc., 9259 Eton Avenue, Chatsworth, Calif., 91311). Other peptide tags useful for purification include, but are not limited to, the hemagglutinin "HA" tag, which corresponds to an epitope derived from the influenza hemagglutinin protein (Wilson et al., 1984, Cell 37:767) and the "Flag" tag.

In other instances, the methods described herein are used to modify a glycoprotein (or an Fc region or Fc fragment containing an N-glycosylation site thereof) that is conjugated to a diagnostic or detectable agent. Such fusion proteins can be useful for monitoring or prognosing the development or progression of disease or disorder as part of a clinical testing procedure, such as determining the efficacy of a particular therapy. Such diagnosis and detection can be accomplished by coupling the glycoprotein to detectable substances including, but not limited to, various enzymes, such as but not limited to horseradish peroxidase, alkaline phosphatase, beta-galactosidase, or acetylcholinesterase; prosthetic groups, such as, but not limited to, streptavidin/biotin and avidin/biotin; fluorescent materials, such as, but not limited to, umbelliforone, fluorescein, fluorescein isothiocynate, rhodamine, dichlorotriazinylamine fluorescein, dansyl chloride or phycoerythrin; luminescent materials, such as, but not limited to, luminol; bioluminescent materials, such as but not limited to, luciferase, luciferin, and aequorin; radioactive materials, such as but not limited to iodine ($^{131}$I, $^{125}$I, $^{123}$I), carbon ($^{14}$C), sulfur ($^{35}$S), tritium ($^{3}$H), indium ($^{115}$In, $^{113}$In, $^{112}$In, $^{111}$In), technetium ($^{99}$Tc), thallium ($^{201}$Ti), gallium ($^{68}$Ga, $^{67}$Ga), palladium ($^{103}$Pd), molybdenum ($^{99}$Mo), xenon ($^{133}$Xe), fluorine ($^{18}$F), $^{153}$SM, $^{177}$Lu, $^{153}$Gd, $^{159}$Gd, $^{149}$Pm, $^{140}$La, $^{175}$Yb, $^{166}$Ho, $^{90}$Y, $^{47}$Sc, $^{186}$Re, $^{188}$Re, $^{142}$Pr, $^{105}$Rh, $^{97}$Ru, $^{68}$Ge, $^{57}$Co, $^{65}$Zn, $^{85}$Sr, $^{32}$P, $^{51}$Cr, $^{54}$Mn, $^{75}$Se, $^{113}$Sn, and $^{117}$Sn; positron emitting metals using various positron emission tomographies, non-radioactive paramagnetic metal ions, and molecules that are radiolabelled or conjugated to specific radioisotopes.

Techniques for conjugating therapeutic moieties to antibodies are well known (see, e.g., Amon et al., "Monoclonal Antibodies For Immunotargeting Of Drugs In Cancer Therapy", in Monoclonal Antibodies And Cancer Therapy, Reisfeld et al. (eds.), pp. 243-56. (Alan R. Liss, Inc. 1985); Hellstrom et al., "Antibodies For Drug Delivery", in Controlled Drug Delivery (2nd Ed.), Robinson et al. (eds.), pp. 623-53 (Marcel Dekker, Inc. 1987)).

II. Sulfated Glycoproteins

In some instances, a modified glycoprotein described herein can be sulfated to a different level (e.g., a higher or lower level) relative to a corresponding wild type or reference glycoprotein. Glycoproteins can be sulfated using, e.g., enzymatic, metabolic, or chemoenzymatic sulfation.

In certain instances, a modified glycoprotein described herein is sulfated using a sulfating enzyme. Enzymes that sulfate polypeptide and/or glycan substrates are generally known. Particular sulfating enzymes include the family of sulfotransferases.

Two general classes of sulfotransferases exist: cytosolic sulfotransferases (Falany et al., FASEB J. 11:206-216 (1997)); and the Golgi-localized, usually membrane-bound sulfotransferases (CHSTs) (Bowman et al., Chem. Biol. 6:R9-R22 (1999)). These sulfotransferases are useful to sulfate glycoproteins according to the disclosure.

The CHST family comprises 14 genes in humans and mice (see, e.g., Rikke et al., Biochim. Biophys. Acta 1307: 331-338 (1996); Hemmerich et al., Glycobiology 10:849-856 (2000); Grunwell et al., Biochem. 41: 13117-13126 (2002)). Such sulfotransferases are commercially available, e.g., from R&D Systems, Inc. (Minneapolis, Minn.). Non-limiting, exemplary CHST sulfotransforases that can be used in the methods disclosed herein include CHSTI (GenBank Accession No. NP_003645), CHST2 (GenBank Accession No. Q9Y4C5), CHST4 (GenBank Accession No. NP_005760), CHST5 (GenBank Accession No. NP_078809), CHST6 (GenBank Accession No. NP_067628), and CHST7 (GenBank Accession No. NP_063939).

In some embodiments, a modified glycoprotein, e.g., a glycosylated antibody, is sulfated after the glycoprotein is produced. For example, a glycoprotein can be recombinantly expressed in a host cell (as described herein), purified using standard methods, and then contacted with a sulfotransferase described herein (e.g., a recombinantly expressed and purified sulfotransferase) under conditions that facilitate sulfation of the purified glycoprotein. In certain embodiments, the conditions include contacting the purified glycoprotein with a sulfotransforase in the presence of a sulfur donor, e.g., 3' phosphoadenosine 5' phosphosulfate (PAPS).

In other sulfation methods, a modified glycoprotein and a sulfotransferase are recombinantly co-expressed in a host cell. The glycoprotein and/or the sulfotransferase can be homologous or heterologous to the host cell. Upon co-expression, the sulfotransferase sulfates the glycoprotein, after which the sulfated glycoprotein can be optionally purified. In some instances, the host cell is genetically engineered to increase sulfation of the recombinantly expressed glycoprotein, such as by introducing, overexpressing, or attenuating the expression of certain enzymes involved in oligosaccharide or endogenous glycoprotein production (see, e.g., U.S. Pat. Nos. 5,047,335; 5,510,261; 5,278,299).

Another method of sulfating modified glycoproteins involves metabolic sulfation. In such methods, sugars are first sulfated chemically and then added to culture media of host cells, which take up the sulfated sugars and incorporate them into glycoproteins.

In one exemplary process, the hydroxyl group of interest is sulfated, and the rest of the hydroxyl groups are acetylated on the carbohydrate. The procedure for the particular sulfated per-acetylated carbohydrate depends on which carbohydrate is of interest and the position of sulfation. Steps can include: 1) protection and de-protection of hydroxyl groups; 2) sulfation of a hydroxyl group using, e.g., pyridine-sulfur trioxide; and 3) per-acetylation of the remaining hydroxyl groups. The process can be accomplished with any combination and sequence of these steps. The sugar sulfates are then neutralized as the calcium salt form, which can then be used directly or changed to another salt form.

Per-O-acetylated versions of both the D- and L-forms of sugars can be sulfated chemically. Nonlimiting examples include 3, 4, 5, 6, or 7 carbon sugars (e.g., glyceraldehyde, erythrose, arabinose, galactose, mannopentulose); keto-sugars (such as fructose); aldo-sugars (such as Glc, Gal, Man); deoxy-sugars (such as fucose, 2-deoxy-glucose, rhamnose); N-acetylated-sugars (such as GlcNAc, ManNAc, GalNAc); reduced sugars (such as mannitol, sorbitol, glycerol); and polysaccharides (such as sucrose, raffinose, N-Acetyl-lactosamine). Specific, nonlimiting examples of sulfated sugars that can be produced using this method are provided in Table 1.

TABLE 1

| Sulfated sugars | |
|---|---|
| Galactose 1-Sulfate | N-Acetyl-Glucosamine 1-Sulfate |
| Galactose 2-Sulfate | N-Acetyl-Glucosamine 3-Sulfate |
| Galactose 3-Sulfate | N-Acetyl-Glucosamine 4-Sulfate |
| Galactose 4-Sulfate | N-Acetyl-Glucosamine 5-Sulfate |
| Galactose 5-Sulfate | N-Acetyl-Glucosamine 6-Sulfate |
| Galactose 6-Sulfate | N-Acetyl-Galactosamine 1-Sulfate |
| Glucose 1-Sulfate | N-Acetyl-Galactosamine 3-Sulfate |
| Glucose 2-Sulfate | N-Acetyl-Galactosamine 4-Sulfate |
| Glucose 3-Sulfate | N-Acetyl-Galactosamine 5-Sulfate |
| Glucose 4-Sulfate | N-Acetyl-Galactosamine 6-Sulfate |
| Glucose 5-Sulfate | N-Acetyl-Mannosamine 1-Sulfate |
| Glucose 6-Sulfate | N-Acetyl-Mannosamine 3-Sulfate |
| Mannose 1-Sulfate | N-Acetyl-Mannosamine 4-Sulfate |
| Mannose 2-Sulfate | N-Acetyl-Mannosamine 5-Sulfate |
| Mannose 3-Sulfate | N-Acetyl-Mannosamine 6-Sulfate |
| Mannose 4-Sulfate | Fucose 1-Sulfate |
| Mannose 5-Sulfate | Fucose 2-Sulfate |
| Mannose 6-Sulfate | Fucose 3-Sulfate |
| Fructose 1-Sulfate | Fucose 4-Sulfate |
| Fructose 3-Sulfate | Fucose 5-Sulfate |
| Fructose 4-Sulfate | |
| Fructose 5-Sulfate | |
| Fructose 6-Sulfate | |

Chemoenzymatic sulfation can also be used to sulfate modified glycoproteins. Briefly, this method involves sulfation of a purified glycan, followed by the incorporation of the sulfated glycan en bloc onto a polypeptide to produce a sulfated glycoprotein.

A glycan can be synthesized de novo using standard techniques or can be obtained from a glycoprotein using an appropriate enzyme, such as an endoglycosidase (e.g., EndoH or EndoF). After sulfation of the glycan, the sulfated glycan can be conjugated to a polypeptide using an appropriate enzyme, such as a transglycosidase, to produce a sulfated glycoprotein.

In one exemplary method, a purified N-glycan is obtained from a glycoprotein using an endoglycosidase. The purified N-glycan is then chemically activated on the reducing end to form a chemically active intermediate. The N-glycan is then further processed, trimmed, and/or glycosylated using appropriate known glycosidases. The glycan is then sulfated, such as using a sulfotransferase described herein. After engineering, the desired N-glycan is transferred onto a glycoprotein using a transglycosidase (such as a transglycosidase in which glycosidic activity has been attenuated using genetically engineering).

The production of sulfated sugars can include the generation of libraries of sulfated sugars having specific sulfation patterns (for example, sugars sulfated on a single epitope, sugars sulfated on two epitopes of biantennaiy glycans, or sugars sulfated at a different carbon positions (e.g., 3-O, 4-O, or 6-O). In some methods, the production of a sulfated glycoprotein includes selecting a particular sulfated sugar from such libraries and conjugating the sulfated sugar to a polypeptide. In other methods, the libraries include mixtures of sulfated sugars, which can be conjugated to polypeptides and the resultant glycoprotein assayed for activity, as described herein.

III. Modulation of Fc Effector Functions

The Fc regions of antibodies interact with cellular receptors to mediate antibody-dependent effector functions. For example, in the case of IgGs, different classes of FcγR mediate various cellular responses, such as phagocytosis by macrophages, antibody-dependent cell-mediated cytotoxicity by NK cells, and degranulation of mast cells. Each FcγR displays different binding affinities and IgG subclass specificities.

Modification of glycoproteins, e.g., mutating one or more amino acid residues disclosed herein, results in modification of glycoprotein function, e.g., Fc region-mediated functions. The effector functions mediated by an antibody Fc region can be divided into two categories. The first type are effector functions that operate after the binding of antibody to an antigen. Such effector functions are mediated by cells of the immune system and include, for example, antibody-dependent cell-mediated cytotoxicity (ADCC) and complement dependent cytotoxicity (CDC) (see, e.g., Daeron, Ann. Rev. Immunol. 15:203-234 (1997); Ward et al., Therapeutic Immunol. 2:77-94 (1995); and Ravetch et al., Ann. Rev. Immunol. 9:457-492 (1991)). The second type are effector functions that operate independently of antigen binding. These include functions that affect half-life, clearance, and the ability to be transferred across cellular barriers by transcytosis (see, e.g., Ward and Ghetie, Therapeutic Immunology 2:77-94 (1995)). Glycoproteins described herein that include a modified Fc region (or a modified effector-mediated portion thereof), such as antibodies, antibody fragments that include a modified Fc region, or glycoprotein conjugates that include a modified Fc region, can mediate these two classes of effector functions. For example, a therapeutic glycoprotein that includes a modified CH2 region (e.g., a modified Fc region) containing a modified glycan as described herein can modify one or more of these effector functions.

In some instances, Fc effector function of a modified glycoprotein containing more than one amino acid residue modification (e.g., two or more mutated Fc region amino acid residues) is equal to or greater than the combination of individual effects exhibited by the individual modifications, relative to a corresponding wild type glycoprotein.

A. Effector Functions Mediated by Fc Receptors

1. Types of Fc Receptors

Several effector functions are mediated by Fc receptors (FcRs), which bind the Fc region of an antibody. Modifying the Fc region of a glycoprotein modifies its ability to bind to FcRs and thus modifies its effector function. Accordingly, methods described herein can be used to modify the activity of a therapeutic glycoprotein.

FcRs are defined by their specificity for immunoglobulin isotypes; Fc receptors for IgG antibodies are referred to as FcγR, for IgE as FcεR, for IgA as FcαR and so on. Four subclasses of FcγR have been identified: FcγRI (CD64), FcγRII (CD32), FcγRIII (CD16), and FcγRIV (see, e.g., Nimmerjahn et al., Immunity 24: 19-28 (2006)). Because each FcγR subclass is encoded by two or three genes, and alternative RNA spicing leads to multiple transcripts, a broad diversity in FcγR isoforms exists. The three genes encoding the FcγRI subclass (FcγRIA, FcγRIB and FcγRIC) are clustered in region 1q21.1 of the long arm of chromosome 1; the genes encoding FcγRII isoforms (FcγRIIA, FcγRIIB and FcγRIIC) and the two genes encoding FcγRIII (FcγRIIIA and FcγRIIIB) are all clustered in region 1q22. These different FcR subtypes are expressed on different cell types (see Ravetch et al., Ann. Rev. Immunol. 9:457-492 (1991)). For example, in humans, FcγRIIIB is found only on neutrophils, whereas FcγRIIIA is found on macrophages, monocytes, natural killer (NK) cells, and a subpopulation of T-cells.

Structurally, the FcγRs are all members of the immunoglobulin superfamily, having an IgG-binding α-chain with an extracellular portion comprised of either two (FcγRI and FcγRIII) or three (FcγRI) Ig-like domains. In addition, FcγRI and FcγRIII have accessory protein chains (γ, ζ) associated with the a-chain, which function in signal transduction. The receptors are also distinguished by their affinity for IgG. FcγRI exhibits a high affinity for IgG, $K_a=10^8-10^9 M^{-1}$ (Ravetch et al., Ann. Rev. Immunol. 19:275-290 (2001)) and can bind monomeric IgG. In contrast FcγRII and FcγRIII show a relatively weaker affinity for monomeric IgG $K_a \leq 10^7 M^{-1}$ (Ravetch et al., Ann. Rev. Immunol. 19:275-290 (2001)), and hence only interact effectively with multimeric immune complexes. FcγRII receptors include FcγRIIA (an "activating receptor") and FcγRIIB (an "inhibiting receptor"), which have similar amino acid sequences that differ primarily in the cytoplasmic domains thereof. Activating receptor FcγRIIA contains an immunoreceptor tyrosine-based activation motif (ITAM) in its cytoplasmic domain. Inhibiting receptor FcγRIIB contains an immunoreceptor tyrosine-based inhibition motif (ITIM) in its cytoplasmic domain (see, e.g., Daeron, Ann. Rev. Immunol. 15:203-234 (1997)). NK-cells carry only FcγRIIIA, and binding of antibodies to FcγRIIIA leads to ADCC activity by the NK cells.

Allelic variants of several of the human FcγR are known to exhibit differences in binding of human and murine IgG, and a number of association studies have correlated clinical outcomes with the presence of specific allelic forms (see Lehmbecher et al., Blood 94:4220-4232 (1999)). Accordingly, modified glycoproteins (e.g., having one or more mutated Fc region amino acid residues) described herein can have altered binding to these allelic variants and can be used as therapeutics for such conditions.

Another type of Fc receptor is the neonatal Fc receptor (FcRn). FcRn is structurally similar to major histocompatibility complex (MHC) and consists of an a-chain noncovalently bound to 2-microglobulin. FcRn has been proposed to regulate homeostasis of IgG in blood as well as possibly control transcytosis across tissues (Ghetie et al., Ann. Rev. Immunol. 18:739-766 (2000)).

2. Cellular Expression of Fc Receptors

Expression of FcRs varies in different immune cells (see Table 2). Modifying a glycoprotein at a CH2 domain of an Fc region (e.g., mutating one or more amino acid residues of an Fc region) affects FcR-mediated binding of the glycoprotein, thereby modulating its effects on different cell types.

TABLE 2

FcγR cellular distribution and effector function

| Receptor Name | Principal antibody ligand | Affinity for ligand | Cell distribution | Effect following binding to antibody |
|---|---|---|---|---|
| FcγRI (CD64) (CD 64) | IgG1 and IgG3 | High (Kd~$10^{-9}$M) | Macrophages Neutrophils Eosinophils Dendritic cells | Phagocytosis Cell activation Activation of respiratory burst Induction of microbe killing |
| FcγRIIA (CD32) | IgG | Low (Kd > $10^{-7}$M) | Macrophages Neutrophils Eosinophils Platelets Langerhans cells | Phagocytosis Degranulation (eosinophils) |
| FcγRIIB1 (CD32) | IgG | Low (Kd > $10^{-7}$M) | B Cells Mast cells | No phagocytosis Inhibition of cell activity |
| FcγRIIB2 (CD32) | IgG | Low (Kd > $10^{-7}$M) | Macrophages Neutrophils Eosinophils | Phagocytosis Inhibition of cell activity |
| FcγRIIIA (CD16a) | IgG | Low (Kd > $10^{-6}$M) | NK cells Macrophages (certain tissues) | Induction of antibody-dependent cell-mediated cytotoxicity (ADCC) Induction of cytokine release by macrophages |
| FcγRIIIB (CD16b) | IgG | Low (Kd > $10^{-6}$M) | Eosinophils Macrophages Neutorphils Mast cells Follicular dendritic cells | Induction of microbe killing |
| FcγRIV | IgG2 | Intermediate | Neutrophils Monocytes Macrophages Dendritic cells | Activation of cell activity |
| FcRn | IgG | | Monocytes Macrophages Dentrite cells Epithelial cells Endothelial cells Hepatocytes | Transfer IgG from a mother to fetus through the placenta Transfers IgG from a mother to infant to milk Protects IgG from degradation |

The 72 kDa extracellular glycoprotein FcγRI is mainly expressed on myeloid cells such as monocytes, macrophages CD4+ progenitor cells and may elicit the ADCC, endocytosis, and phagocytosis responses (Siberil et al., 2006, J Immunol Lett 106:111-118). The 40 kDa FcγRII group of receptors (A, B and C isoforms) exhibit extracellular domains but do not contain active signal transduction domains. The FcγRIIA is mainly expressed on monocytes, macrophages, neutrophils, and platelets, whereas the FcγRIIC receptor has only been identified on NK cells. These two receptors have been shown to initiate ADCC, endocytosis, phagocytosis and inflammatory mediator release (Cassel et al., 1993. Mol Immunol 30:451-60). By contrast, the FcγRIIB (B1 and B2 types) receptors are expressed on B cells, Mast cells, basophils, monocytes, macrophages and dendritic cells and have been shown to downregulate the immune responses triggered by the A and C isoforms.

The 50 kDa FcγRIIIA is expressed on NK cells, monocytes, macrophages and a subset of T lymphocytes, where it activates ADCC, phagocytosis, endocytosis and cytokine release (Gessner et al., 1998, Ann Hematology 76:231-48). The FcγRIIIB isoform is a glycosyl-phosphatidylinositol (GPI) anchored peripheral membrane protein involved in the degranulation and the production of reactive oxygen intermediates (Salmon et al., 1995 J. Clin. Inves. 95:2877-2885).

3. Binding Properties of Modified Glycoproteins

The modified glycoproteins of the disclosure can have altered FcR and/or Clq binding properties (e.g., binding specificity, equilibrium dissociation constant (KD), dissociation and association rates ($K_{off}$ and $K_{on}$ respectively), binding affinity and/or avidity), relative to a corresponding wild type glycoprotein. One skilled in the art can determine which kinetic parameter is most important for a given application. For example, the modified glycoproteins described herein can have reduced binding to one or more activating Fc receptor (e.g., FcγRIIIA) and/or enhanced binding to an inhibitory Fc receptor (e.g., FcγRIM) and thus exhibit reduced ADCC activity. Alternatively, the modified glycoproteins can have increased binding to one or more activating Fc receptor (e.g., FcγRIIIA) and/or reduced binding to an inhibitory Fc receptor (e.g., FcγRITB) and thus have increased ADCC activity. The ratio of binding affinities (e.g., equilibrium dissociation constants (KD)) can indicate if the ADCC activity of a modified glycoprotein is enhanced or decreased. Additionally, the modified glycoproteins described herein can have reduced binding to Clq (and to reduce or eliminate CDC activity), or increased binding to Clq (and to increase CDC activity).

The affinities and binding properties of an Fc region for an FcR and/or Clq can be measured by a variety of in vitro assay methods known in the art for determining Fc-FcγR interactions. Nonlimiting examples of such methods include equilibrium methods (e.g., enzyme-linked immunoabsorbent assay (ELISA) or radioimmunoassay (RIA)), kinetics (e.g., BIACORE® analysis), indirect binding assays, competitive inhibition assays, fluorescence resonance energy transfer (FRET), gel electrophoresis, and chromatography (e.g., gel filtration). These and other methods can use a label on one or more of the components being examined and/or employ a variety of detection methods including, but not limited to, chromogenic, fluorescent, luminescent, or isotopic labels.

In some instances, a modified glycoprotein exhibits reduced binding affinity for one or more Fc receptors including, but not limited to FcγRI (CD64) including isoforms FcγRIA, FcγRIB, and FcγRIC; FcγRII (CD32 including isoforms FcγRIIA, FcγRIIB, and FcγRIIC); and FcγRITT (CD16, including isoforms FcγRIIIA and FcγRIIIB), relative to a corresponding wild type glycoprotein. In certain embodiments, a modified glycoprotein does not have increased binding to FcγRIIB receptor as compared to a corresponding wild type glycoprotein.

In other instances, a modified glycoprotein exhibits increased binding affinity for one or more Fc receptors including, but not limited to FcγRI (CD64) including isoforms FcγRIA, FcγRIB, and FcγRIC; FcγRII (CD32 including isofomis FcγrRIIA, FcγRIIB, and FcγRIIC); and FcγRIII (CD16, including isoforms FcγRIIIA and FcγRIIIB), relative to a corresponding wild type glycoprotein. In certain embodiments, a modified glycoprotein has increased binding to FcγRIIB receptor as compared to a corresponding wild type glycoprotein.

In one embodiment, a modified glycoprotein exhibits decreased binding affinity to FcγRI relative to a corresponding wild type glycoprotein. In another embodiment, a modified glycoprotein exhibits a binding affinity for FcγRI receptor that is at least 1.2 fold, 1.5 fold, 1.8 fold, 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than a corresponding wild type glycoprotein. In another embodiment, a modified glycoprotein exhibits an affinity for FcγRI receptor that is at least 90%, at least 80%, at least 70%, at least 60%, at least 50%, at least 40%, at least 30%, at least 20%, at least 10%, or at least 5% less than a corresponding wild type glycoprotein.

In other embodiments, a modified glycoprotein exhibits increased binding affinity to FcγRI relative to a corresponding wild type glycoprotein. In another embodiment, a modified glycoprotein exhibits a binding affinity for FcγRI receptor that is at least 1.2 fold, 1.5 fold, 1.8 fold, 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold higher than a corresponding wild type glycoprotein. In another embodiment, a modified glycoprotein exhibits an affinity for FcγRI receptor that is at least 5%, at least 10%, at least 20%, at least 30%, at least 40%, at least 50%, at least 60%, at least 70%, at least 80%, or at least 90% higher than a corresponding wild type glycoprotein.

In one embodiment, a modified glycoprotein exhibits decreased affinity for the FcγRIIIA receptor relative to a corresponding wild type glycoprotein. In another embodiment, a modified glycoprotein exhibits an affinity for FcγRIIIA receptor that is at least 1.2 fold, 1.5 fold, 1.8 fold, 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than a corresponding wild type glycoprotein. In another embodiment, a modified glycoprotein exhibits an affinity for FcγRIIIA receptor that is at least 90%, at least 80%, at least 70%, at least 60%, at least 50%, at least 40%, at least 30%, at least 20%, at least 10%, or at least 5% less than a corresponding wild type glycoprotein.

In other embodiments, a modified glycoprotein exhibits increased affinity for the FcγRIIIA receptor relative to a corresponding wild type glycoprotein. In another embodiment, a modified glycoprotein exhibits an affinity for FcγRIIIA receptor that is at least 1.2 fold, 1.5 fold, 1.8 fold, 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold greater than a corresponding wild type glycoprotein. In another embodiment, a modified glycoprotein exhibits an affinity for FcγRIIIA receptor that is at least 90%, at least 80%, at least 70%, at least 60%, at least 50%, at least 40%, at least 30%, at least 20%, at least 10%, or at least 5% greater than a corresponding wild type glycoprotein.

The F158V allelic variant of the FcγRIIIA receptor has altered binding characteristics to antibodies. In one embodiment, a modified glycoprotein binds with decreased affinity to FcγRIIIA (F 158V) relative to a corresponding wild type glycoprotein. In another embodiment, a modified glycoprotein exhibits an affinity for FcγRIIIA (F158V) receptor that is at least 1.2 fold, 1.5 fold, 1.8 fold, 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than that of a corresponding wild type glycoprotein. In another embodiment, a modified glycoprotein exhibits an affinity for the FcγRIIIA (F158V) receptor that is at least 90%, at least 80%, at least 70%, at least 60%, at least 50%, at least 40%, at least 30%, at least 20%, at least 10%, or at least 5% less than a corresponding wild type glycoprotein.

In other embodiments, a modified glycoprotein binds with increased affinity to FcγRIIIA (F158V) relative to a corresponding wild type glycoprotein. In another embodiment, a modified glycoprotein exhibits an affinity for FcγRIIIA (F158V) receptor that is at least 1.2 fold, 1.5 fold, 1.8 fold, 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold higher than that of a corresponding wild type glycoprotein. In another embodiment, a modified glycoprotein exhibits an affinity for the FcγRIIIA (F158V) receptor that is at least 90%, at least 80%, at least 70%, at least 60%, at least 50%, at least 40%, at least 30%, at least 20%, at least 10%, or at least 5% higher than a corresponding wild type glycoprotein.

In another embodiment, a modified glycoprotein exhibits an increased affinity for the FcγRIIB receptor as compared to a corresponding wild type glycoprotein. In another embodiment, a modified glycoprotein exhibits an affinity for the FcγRIIB receptor that is unchanged or increased by at least at least 1.2 fold, 1.5 fold, 1.8 fold, 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold than that of a corresponding wild type glycoprotein. In another embodiment, a modified glycoprotein exhibits an affinity for the FcγRIIB receptor that is increased by at least 5%, at least 10%, at least 20%, at least 30%, at least 40%, at least 50%, at least 60%, at least 70%, at least 80%, at least 90%, or at least 95% relative to a corresponding wild type glycoprotein.

In other embodiments, a modified glycoprotein exhibits a decreased affinity for the FcγRIIB receptor as compared to a corresponding wild type glycoprotein. In another embodiment, a modified glycoprotein exhibits an affinity for the FcγRIIB receptor that is decreased by at least at least 1.2 fold, 1.5 fold, 1.8 fold, 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold than that of a corresponding wild type glycoprotein. In another embodiment, a modified glycoprotein exhibits an affinity for the FcγRIIB receptor that is decreased by at least 5%, at least 10%, at least 20%, at least 30%, at least 40%, at least 50%, at least 60%, at least 70%, at least 80%, at least 90%, or at least 95% relative to a corresponding wild type glycoprotein.

In another embodiment, a modified glycoprotein exhibits an affinity for the FcγRI, FcγRIIIA, or FcγRIIIA (F158V) receptor that is about 100 nM to about 100 μM, or about 100 nM to about 10 μM, or about 100 nM to about 1 μM, or about 1 nM to about 100 μM, or about 10 nM to about 100 μM, or about 1 μM to about 100 μM, or about 10 μM to about 100 μM. In certain embodiments, a modified glycoprotein exhibits an affinity for the FcγRI, FcγRIIIA, or FcγRIIIA (F158V) receptor that is greater than about 1 μM, greater than about 5 μM, greater than about 10 μM, greater than about 25 μM, greater than about 50 μM, or greater than about 100 μM.

In another embodiment, a modified glycoprotein exhibits an affinity for the FcγRIIB receptor that is about 100 nM to about 100 μM, or about 100 nM to about 10 μM, or about 100 nM to about 1 μM, or about 1 nM to about 100 μM, or about 10 nM to about 100 μM, or about 1 μM to about 100 μM, or about 10 μM to about 100 μM. In certain embodiments, a modified glycoprotein exhibits an affinity for the FcγRI, FcγRIIIA, or FcγRIIIA (F158V) receptor that is less than about 100 μM, less than about 50 μM, less than about 10 μM, less than about 5 μM, less than about 2.5 μM, less than about 1 μM, less than about 100 nM, or less than about 10 nM.

In other embodiments, a modified glycoprotein exhibits an affinity for the FcγRIIB receptor that is between about 100 nM to about 100 μM, or about 100 nM to about 10 μM, or about 100 nM to about 1 μM, or about 1 nM to about 100 μM, or about 10 nM to about 100 μM, or about 1 μM to about 100 μM, or about 10 μM to about 100 μM. In certain embodiments, a modified glycoprotein exhibits an affinity for the FcγRI, FcγRIIIA, or FcγRIIIA (F158V) receptor that is less than about 100 μM, less than about 50 μM, less than about 10 μM, less than about 5 μM, less than about 2.5 μM, less than about 1 μM, less than about 100 nM, or less than about 10 nM.

4. Modification of ADCC Activity

The modified glycoproteins described herein can have modified ability to induce antibody-dependent cell-mediated cytotoxicity ("ADCC"), relative to a corresponding wild type glycoprotein. ADCC refers to a form of cytotoxicity in which secreted Ig bound to Fc receptors (FcRs) present on certain cytotoxic cells (e.g., Natural Killer (NK) cells, neutrophils, and macrophages) enables these cytotoxic effector cells to bind specifically to an antigen-bearing target cell and subsequently kill the target cell with cytotoxins. Specific high-affinity IgG antibodies directed to the surface of target cells "arm" the cytotoxic cells and are required for such killing. Lysis of the target cell is extracellular, requires direct cell-to-cell contact, and does not involve complement.

The ability of a glycoprotein to mediate lysis of the target cell by ADCC can be assayed using known methods. For example, to assess ADCC activity, a modified glycoprotein described herein can be added to target cells in combination with immune effector cells, which can be activated by an antigen antibody complex, resulting in cytolysis of the target cell. Cytolysis can be detected, such as by detecting the release of a label (e.g., radioactive substrates, fluorescent dyes or natural intracellular proteins) from the lysed cells. Useful effector cells for such assays include peripheral blood mononuclear cells (PBMC) and Natural Killer (NK) cells. Specific examples of in vitro ADCC assays are described in Wisecarver et al., 1985 79:277-282; Bruggemann et al., 1987, J Exp Med 166:1351-1361; Wilkinson et al., 2001, J Immunol Methods 258:183-191; Patel et al., 1995 J Immunol Methods 184:29-38. ADCC activity can also be assessed in vivo, e.g., in an animal model, such as that disclosed in Clynes et al., 1998, PNAS USA 95:652-656.

In one embodiment, a modified glycoprotein exhibits decreased ADCC activity relative to a corresponding wild type glycoprotein. In some embodiments, a modified glycoprotein exhibits ADCC activity that is at least 1.2 fold, 1.5 fold, 1.8 fold, 2 fold, or at least 3 fold, or at least 5 fold, or at least 10 fold, or at least 50 fold, or at least 100 fold less than that of a corresponding wild type glycoprotein. In still another embodiment, a modified glycoprotein exhibits ADCC activity that is reduced by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to a corresponding wild type glycoprotein. In certain embodiments, a modified glycoprotein exhibits no detectable ADCC activity.

In other embodiments, a modified glycoprotein exhibits increased ADCC activity relative to a corresponding wild type glycoprotein. In some embodiments, a modified glycoprotein exhibits ADCC activity that is at least 1.2 fold, 1.5 fold, 1.8 fold, 2 fold, or at least 3 fold, or at least 5 fold, or at least 10 fold, or at least 50 fold, or at least 100 fold higher than that of a corresponding wild type glycoprotein. In still another embodiment, a modified glycoprotein exhibits ADCC activity that is increased by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to a corresponding wild type glycoprotein.

B. Effector Functions Mediated by Complement

Another antibody effector function is "complement dependent cytotoxicity", or "CDC", which refers to a biochemical event of antibody-mediated target cell destruction by the complement system. The complement system is a complex system of proteins found in normal blood plasma that combines with antibodies to destroy pathogenic bacteria and other foreign cells.

1. Clq Binding

Clq and two serine proteases, Clr and Cls, form the complex Cl, the first component of the CDC pathway, and Fc binding to C1q mediates CDC (see Ward et al., Therapeutic Immunology 2:77-94 (1995)).

In one embodiment, a modified glycoprotein exhibits decreased affinity to C1q relative to a corresponding wild type glycoprotein. In another embodiment, a modified glycoprotein exhibits an affinity for C1q that is at least 1.2 fold, 1.5 fold, 1.8 fold, 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold less than a corresponding wild type glycoprotein. In another embodiment, a modified glycoprotein exhibits an affinity for C1q that is at least 90%, at least 80%, at least 70%, at least 60%, at least 50%, at least 40%, at least 30%, at least 20%, at least 10%, or at least 5% less than a corresponding wild type glycoprotein.

In other embodiments, a modified glycoprotein exhibits increased affinity to C1q relative to a corresponding wild type glycoprotein. In another embodiment, a modified glycoprotein exhibits an affinity for C1q that is at least 1.2 fold, 1.5 fold, 1.8 fold, 2 fold, or at least 3 fold, or at least 5 fold, or at least 7 fold, or a least 10 fold, or at least 20 fold, or at least 30 fold, or at least 40 fold, or at least 50 fold, or at least 60 fold, or at least 70 fold, or at least 80 fold, or at least 90 fold, or at least 100 fold, or at least 200 fold higher than a corresponding wild type glycoprotein. In another embodiment, a modified glycoprotein exhibits an affinity for C1q that is at least 90%, at least 80%, at least 70%, at least 60%, at least 50%, at least 40%, at least 30%, at least 20%, at least 10%, or at least 5% higher than a corresponding wild type glycoprotein.

In another embodiment, a modified glycoprotein exhibits an affinity for C1q that is about 100 nM to about 100 µM, or about 100 nM to about 10 µM, or about 100 nM to about 1 µM, or about 1 nM to about 100 µM, or about 10 nM to about 100 µM, or about 1 to about 100 µM, or about 10 µM to about 100 µM. In certain embodiments, a modified glycoprotein exhibits an affinity for C1q that is greater than about 1 greater than about 5 greater than about 10 µM, greater than about 25 µM, greater than about 50 µM, or greater than about 100 µM.

2. CDC Activity Mediated by Modified Glycoproteins

In some embodiments, a modified glycoprotein described herein can exhibit a modified level of complement activation, e.g., relative to a corresponding wild type glycoprotein. Any known CDC assay (such as described, e.g., in Gazzano-Santoro et al., 1996, J. Immunol. Methods, 202: 163), can be performed to assess complement activation. In one nonlimiting, exemplary method, various concentrations of glycoprotein (modified or wild type) and human complement are diluted with buffer. Cells that express the antigen to which the glycoprotein binds arc diluted to a density of about $1 \times 10^6$ cells/mL. Mixtures of glycoprotein (modified or wild type), diluted human complement, and cells expressing the antigen are added to a flat bottom tissue culture 96 well plate and allowed to incubate for 2 hrs at 37° C. and 5% $CO_2$ to facilitate complement mediated cell lysis. 50 µL of alamar blue (Accumed International) is then added to each well and incubated overnight at 37° C. The absorbance is measured using a 96-well fluorometer with excitation at 530 nm and emission at 590 nm. The results can be expressed in relative fluorescence units (RFU). The sample concentrations can be computed from a standard curve, and the percent activity of the modified glycoprotein is compared to that of the corresponding wild type glycoprotein. A difference in the percent activity of the modified glycoprotein compared to that of the corresponding wild type glycoprotein indicates that the modified glycoprotein exhibits a modified level of complement activation, e.g., relative to a corresponding wild type glycoprotein.

In one embodiment, a modified glycoprotein exhibits decreased CDC activity relative to a corresponding wild type glycoprotein. In another embodiment, a modified glycoprotein exhibits CDC activity that is at least 1.2 fold, 1.5 fold, 1.8 fold, 2 fold, or at least 3 fold, or at least 5 fold, or at least 10 fold, or at least 50 fold, or at least 100 fold less than that of a corresponding wild type glycoprotein. In still another embodiment, a modified glycoprotein exhibits CDC activity that is reduced by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to a corresponding wild type glycoprotein. In certain embodiments, a modified glycoprotein exhibits no detectable CDC activity.

In other embodiments, a modified glycoprotein exhibits increased CDC activity relative to a corresponding wild type glycoprotein. In another embodiment, a modified glycoprotein exhibits CDC activity that is at least 1.2 fold, 1.5 fold, 1.8 fold, 2 fold, or at least 3 fold, or at least 5 fold, or at least 10 fold, or at least 50 fold, or at least 100 fold higher than that of a corresponding wild type glycoprotein. In still another embodiment, a modified glycoprotein exhibits CDC activity that is increased by at least 10%, or at least 20%, or by at least 30%, or by at least 40%, or by at least 50%, or by at least 60%, or by at least 70%, or by at least 80%, or by at least 90%, or by at least 100%, or by at least 200%, or by at least 300%, or by at least 400%, or by at least 500% relative to a corresponding wild type glycoprotein.

C. Other Properties of Modified Glycoproteins

Modifying glycoproteins as described herein results in glycoproteins with modified clearance, half-life, apoptosis, and/or phagocytosis, relative to corresponding wild type glycoproteins. For example, a modified glycoprotein can have altered binding affinity for FcRn, and thus altered clearance/half-life properties (see, e.g., D'Acqua et al., J. Immunol. 169:1571-1580 (2002)).

IV. Recombinant Gene Expression

In accordance with the present disclosure, there may be employed conventional molecular biology, microbiology, and recombinant DNA techniques within the skill of the art. Such techniques are described in the literature (see, e.g., Sambrook, Fritsch & Maniatis, Molecular Cloning: A Laboratory Manual, Second Edition (1989) Cold Spring Harbor Laboratory Press, Cold Spring Harbor, N.Y.; DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins eds. (1985)); Transcription And Translation (B. D. Hames & S. J. Higgins, eds. (1984)); Animal Cell Culture (R. I. Freshney, ed. (1986)); Immobilized Cells and Enzymes (IRL Press, (1986)); B. Perbal, A Practical Guide To Molecular Cloning (1984); F. M. Ausubel et al. (eds.), Current Protocols in Molecular Biology, John Wiley & Sons, Inc. (1994).

Recombinant expression of a gene, such as a gene encoding a polypeptide, such as a modified antibody or a sulfotransferase described herein, can include construction of an expression vector containing a polynucleotide that encodes the modified polypeptide. Once a polynucleotide has been obtained, a vector for the production of the modified polypeptide can be produced by recombinant DNA technology using techniques known in the art. Known methods can be used to construct expression vectors containing polypeptide coding sequences and appropriate transcriptional and translational control signals. These methods include, for example, in vitro recombinant DNA techniques, synthetic techniques, and in vivo genetic recombination.

An expression vector can be transferred to a host cell by conventional techniques, and the transfected cells can then cultured by conventional techniques to produce modified polypeptides.

A variety of host expression vector systems can be used (see, e.g., U.S. Pat. No. 5,807,715). Such host-expression systems can be used to produce polypeptides and, where desired, subsequently purified. Such host expression systems include microorganisms such as bacteria (e.g., E. coli and B. subtilis) transformed with recombinant bacteriophage DNA, plasmid DNA or cosmid DNA expression vectors containing polypeptide coding sequences; yeast (e.g., Saccharomyces and Pichia) transformed with recombinant yeast expression vectors containing polypeptide coding sequences; insect cell systems infected with recombinant virus expression vectors (e.g., baculovirus) containing polypeptide coding sequences; plant cell systems infected with recombinant virus expression vectors (e.g., cauliflower mosaic virus, CaMV; tobacco mosaic virus, TMV) or transformed with recombinant plasmid expression vectors (e.g. Ti plasmid) containing polypeptide coding sequences; or mammalian cell systems (e.g., COS, CHO, BHK, 293, NSO, and 3T3 cells) harboring recombinant expression constructs containing promoters derived from the genome of mammalian cells (e.g., metallothionein promoter) or from mammalian viruses (e.g., the adenovirus late promoter; the vaccinia virus 7.5K promoter).

For bacterial systems, a number of expression vectors can be used, including, but not limited to, the E. coli expression vector pUR278 (Ruther et al., 1983, EMBO 12:1791); pIN vectors (Inouye & Inouye, 1985, Nucleic Acids Res. 13:3101-3109; Van Heeke & Schuster, 1989, J. Biol. Chem. 24:5503-5509); and the like. pGEX vectors can also be used to express foreign polypeptides as fusion proteins with glutathione 5-transferase (GST).

For expression in mammalian host cells, viral-based expression systems can be utilized (see, e.g., Logan & Shenk, 1984, Proc. Natl. Acad. Sci. USA 8 1:355-359). The efficiency of expression can be enhanced by the inclusion of appropriate transcription enhancer elements, transcription terminators, etc. (see, e.g., Bittner et al., 1987, Methods in Enzymol. 153:516-544).

In addition, a host cell strain can be chosen that modulates the expression of the inserted sequences, or modifies and processes the gene product in the specific fashion desired. Different host cells have characteristic and specific mechanisms for the post-translational processing and modification of proteins and gene products. Appropriate cell lines or host systems can be chosen to ensure the correct modification and processing of the polypeptide expressed. Such cells include, for example, established mammalian cell lines and insect cell lines, animal cells, fungal cells, and yeast cells. Mammalian host cells include, but are not limited to, CHO, VERY, BHK, HeLa, COS, MDCK, 293, 3T3, W138, BT483, Hs578T, HTB2, BT20 and T47D, NSO (a murine myelorna cell line that does not endogenously produce any immunoglobulin chains), CRL7030 and HsS78Bst cells.

For long-term, high-yield production of recombinant proteins, host cells are engineered to stably express a polypeptide. Host cells can be transformed with DNA controlled by appropriate expression control elements known in the art, including promoter, enhancer, sequences, transcription terminators, polyadenylation sites, and selectable markers. Methods commonly known in the art of recombinant DNA technology can be used to select a desired recombinant clone.

Once a modified glycoprotein described herein been produced by recombinant expression, it may be purified by any method known in the art for purification, for example, by chromatography (e.g., ion exchange, affinity, and sizing column chromatography), centrifugation, differential solubility, or by any other standard technique for the purification of proteins. For example, an antibody can be isolated and purified by appropriately selecting and combining affinity columns such as Protein A column with chromatography columns, filtration, ultra filtration, salting-out and dialysis procedures (see Antibodies: A Laboratory Manual, Ed Harlow, David Lane, Cold Spring Harbor Laboratory, 1988). Further, as described herein, a glycoprotein can be fused to heterologous polypeptide sequences to facilitate purification. Glycoproteins having desired sugar chains can be separated with a lectin column by methods known in the art (see, e.g., WO 02/30954).

V. Pharmaceutical Compositions and Administration

A modified glycoprotein described herein can be incorporated into a pharmaceutical composition. Such a pharmaceutical composition is useful as an improved composition for the prevention and/or treatment of diseases relative to the corresponding wild type glycoprotein. Pharmaceutical compositions comprising a modified glycoprotein can be formulated by methods known to those skilled in the art (see, e.g., Remington's Pharmaceutical Sciences pp. 1447-1676 (Alfonso R. Gennaro, ed., 19th ed. 1995)). The pharmaceutical composition can be administered parenterally in the form of an injectable formulation comprising a sterile solution or suspension in water or another pharmaceutically acceptable liquid. For example, the pharmaceutical composition can be formulated by suitably combining the sulfated glycoprotein with pharmaceutically acceptable vehicles or media, such as sterile water and physiological saline, vegetable oil, emulsifier, suspension agent, surfactant, stabilizer, flavoring excipient, diluent, vehicle, preservative, binder, followed by mixing in a unit dose form required for generally accepted pharmaceutical practices. The amount of active ingredient included in the pharmaceutical preparations is such that a suitable dose within the designated range is provided.

The sterile composition for injection can be formulated in accordance with conventional pharmaceutical practices using distilled water for injection as a vehicle. For example, physiological saline or an isotonic solution containing glucose and other supplements such as D-sorbitol, D-mannose, D-mannitol, and sodium chloride may be used as an aqueous solution for injection, optionally in combination with a suitable solubilizing agent, for example, alcohol such as ethanol and polyalcohol such as propylene glycol or polyethylene glycol, and a nonionic surfactant such as polysorbate 80™, HC0-50 and the like.

Nonlimiting examples of oily liquid include sesame oil and soybean oil, and it may be combined with benzyl benzoate or benzyl alcohol as a solubilizing agent. Other items that may be included are a buffer such as a phosphate buffer, or sodium acetate buffer, a soothing agent such as procaine hydrochloride, a stabilizer such as benzyl alcohol or phenol, and an antioxidant. The formulated injection can be packaged in a suitable ampule.

Route of administration can be parenteral, for example, administration by injection, transnasal administration, transpulmonary administration, or transcutaneous administration. Administration can be systemic or local by intravenous injection, intramuscular injection, intraperitoneal injection, subcutaneous injection.

A suitable means of administration can be selected based on the age and condition of the patient. A single dose of the pharmaceutical composition containing a modified glycoprotein can be selected from a range of 0.001 to 1000 mg/kg of body weight. On the other hand, a dose can be selected in the range of 0.001 to 100000 mg/body weight, but the present disclosure is not limited to such ranges. The dose and method of administration varies depending on the weight, age, condition, and the like of the patient, and can be suitably selected as needed by those skilled in the art.

All publications, patent applications, patents, and other references mentioned herein are incorporated by reference in their entirety. In addition, the materials, methods, and examples are illustrative only and not intended to be limiting. Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described herein.

The disclosure is further illustrated by the following examples. The examples are provided for illustrative purposes only. They are not to be construed as limiting the scope or content of the disclosure in any way.

EXAMPLES

Example 1—Generation of Mutant Antibodies

Various double mutants were made by synthesizing the heavy chain gene of rituximab, using its nucleotide sequence that was first codon-optimized using DNA2.0. The amino acids to be mutated were picked based on their molecular interactions found in the crystal structures for Fc dimers with glycans bound to Fc-gamma receptor III (Mizushima et al., Genes to Cells 16:1071-1080 (2011), and Ferrara et al., PNAS 108:12669-12674 (2011)). The antibody genes were expressed using the CMV promoter in either HEK293 or CHO-S cells along with the synthesized gene for the light chain expressed from a separate plasmid. The antibodies were transiently expressed from the two plasmids and purified by protein G chromatography. The amino acid sequences of wild type rituximab heavy chain and mutants 1, 2, 3, and 4 are depicted in FIGS. 2A-2E.

Example 2—Characterization of Glycosylation of Mutant Antibodies

IgG1 glycosylation typically includes complex type N-glycans with variable galactosylation and low levels of sialylation, as well as low levels of high mannose and hybrid glycans. The lack of complexity can be, in part, the result of steric hindrance, which may limit access of some glycosyltransferase enzymes. While not wishing to be bound by theory, it is believed that the introduction of certain backbone mutations to a glycoprotein as described herein may relieve the hydrogen bonding and Van Der Waals forces between the glycans of the glycoprotein and the backbone amino acids, resulting in the ability to produce modifications to glycan composition during protein expression, e.g., by a host cell expressing the glycoprotein, and/or by post-production, in vitro methods.

Glycosylation was characterized by LC-MS/MS analysis of the glycopeptides generated by tryptic digestion of the protein after reduction (with DTT) and alkylation (with TAM). Identification of the glycans was based on $MS^2$ fragmentation, and quantitation was performed by extracting the mass of the $[M+3H]^{3+}$ ion.

Figure 3:
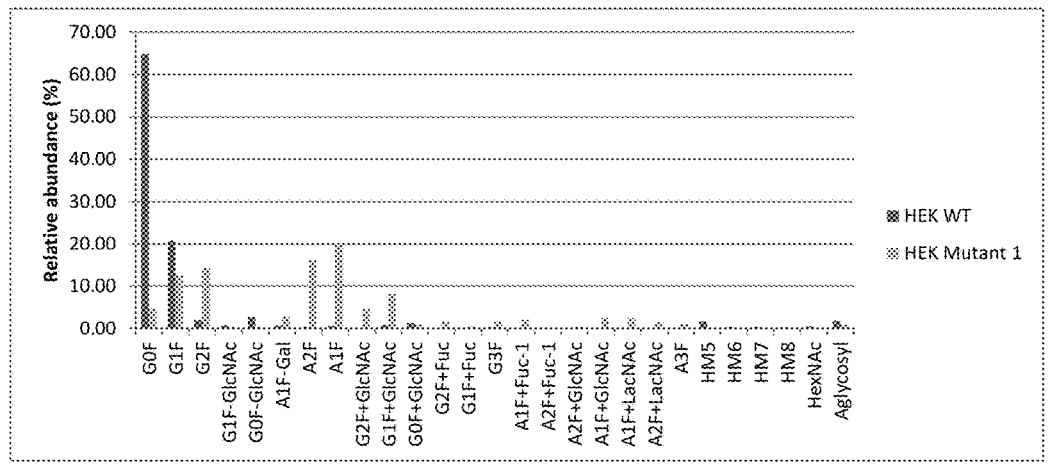
FIG. 3 is a graphical representation of glycosylation patterns of wild type (WT) and mutant 1 of rituximab IgG antibody expressed in HEK293 cells.

FIG. 3 shows a comparison of the glycosylation of wild type rituximab and that of mutant 1 (F241A, F243A) expressed in HEK293 cells. As shown in FIG. 3, compared to wild type rituximab, sialylation is increased in the mutant, as are levels of antennary fucose and bisecting N-acetylglucosamine.

Figure 4:
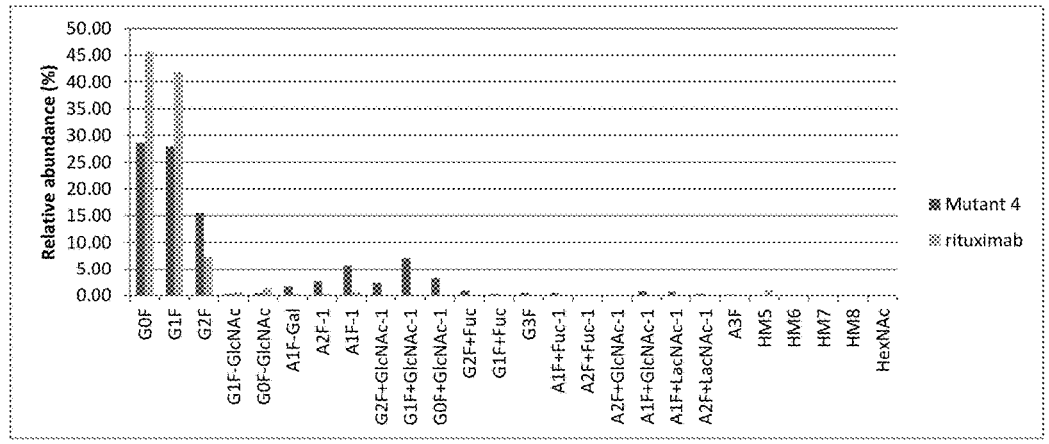
FIG. 4 is a graphical representation of glycosylation patterns of wild type and mutant 4 of rituximab IgG1 antibody expressed in HEK293 cells.

FIG. 4 shows a comparison of the glycosylation of wild type rituximab and that of mutant 4 (T260A, R301A) expressed in HEK293 cells. Detailed analytical characterization showed that the glycans of mutant 4 were quite different from the glycans of WT antibody expressed in the same HEK cells. There was a significant decrease of G0F and G1F species in mutant 4, and an increase in G2F and sialalylated species. Furthermore, glycan structures that are not typically observed in monoclonal antibodies (such as triantennary, bisecting N-acetylglucosamine, and antennary fucosylation) were observed in mutant 4. Thus, mutating amino acid residues within the Fc region leads to increased glycan complexity.

Example 3—Characterization of Effector Functions of Mutant Antibodies

Effector functions of rituximab and mutant 4 were determined using cell-based assays measuring antibody dependent cytotoxicity (ADCC) and antibody dependent phagocytosis (ADPC).

ADCC

ADCC assays were performed using freshly isolated human PBMC as a source of effector cells. Briefly, PBMC's were isolated from the human peripheral blood of healthy donors by Ficoll gradient. Antibody samples (wild type rituximab and mutant 4) were diluted in X-VIVO medium at varying concentrations, and both target (Raji) and effector (PBMC's) cells were washed in X-VIVO medium by repeated centrifugation/aspiration.

Raji cells were reconstituted to $0.6 \times 10^6$ cells/ml in X-VIVO medium, and 100 µl were added to each well of a 96 well U-bottom plate. Then 20 µl of diluted wild type rituximab or mutant 4 were added to target cells and incubated at 37° C./5% $CO_2$/humid air for 15 min. Effector (PBMC's) cells were added to wells at a 24:1, or 36:1 (E:T ratio) and then incubated for 4 hrs at 37° C./5% $CO_2$/humid air to induce cell killing. Assay plates were tested for LOH activity as a measure of cell lysis.

Cytotoxic activity of mutant 4 was significantly lower compared to wild type rituximab. Both efficacy and potency was greatly diminished, with mutant 4 having only 17% potency compared to wild type. The $EC_{50}$ of wild type rituximab was 46 ng/ml, and 289 ng/ml for mutant 4.

ADPC

To assay ADPC, human PBMCs were isolated from whole blood by a Ficoll gradient. The monocyte population was purified by negative selection using a cocktail of lineage specific monoclonal antibodies and magnetic beads. Macrophages were polarized in the presence of cytokines (M-CSF for M2 macrophages, and GM-CSF for M1 macrophages) for 6 days. Both macrophage populations were used as effector cells (E) to measure their phagocytic activity in presence of antibodies. Raji cells expressing CD20 were used as target cells (T).

Macrophages were incubated with Raji cells (E:T, 4:1 in the presence of wild type rituximab or mutant 4 for 4 hrs, after which phagocytosis was measured by fluorocytometry as a fraction of doubly stained cells. Phagocytic activity was measured and quantified as a fraction of macrophages associated with target cells.

Figure 7:
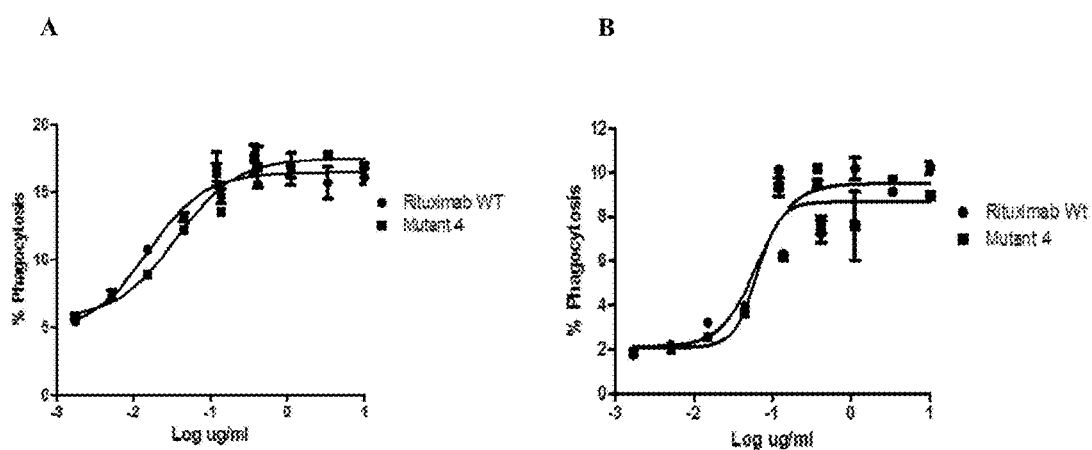
FIG. 7 depicts graphical representations of the effect of wild-type rituximab and mutant 4 on M2 (A) and M1 (B) macrophage-mediated cytosis.

FIG. 7 depicts a dose-response curve of M1 (FIG. 7B) and M2 (FIG. 7A) mediated phagocytosis in the presence of wild type rituximab and mutant 4. Both wild type rituximab and mutant 4 induced comparable phagocytic responses: potency and efficacy by both populations of macrophages. Comparable results were observed using several donors.

These data demonstrate that the amino acid substitutions in mutant 4 (T260A, R301A) did not have any measurable effect on phagocytosis. That ADCC activity (mediated primarily by FcγRIIIa on NK cells) was greatly diminished by the amino acid substitutions in mutant 4, while the same mutations did not have any effect on phagocytosis (mediated primarily by FcγRII activating and inhibitory receptors), demonstrates the altered specificity for different Fc receptors and cell types induced by mutation.

C1q Binding

C1q binding affinities were determined for wild type rituximab and mutant 4. C1q is one of the proteins in the complement cascade and is used as a proxy to assess potential CDC activity. Interestingly, mutant 4 had a 3-fold lower binding efficiency compared to wild type rituximab, suggesting an effect of the mutation on decreasing complement activation as well.

Figure 5:
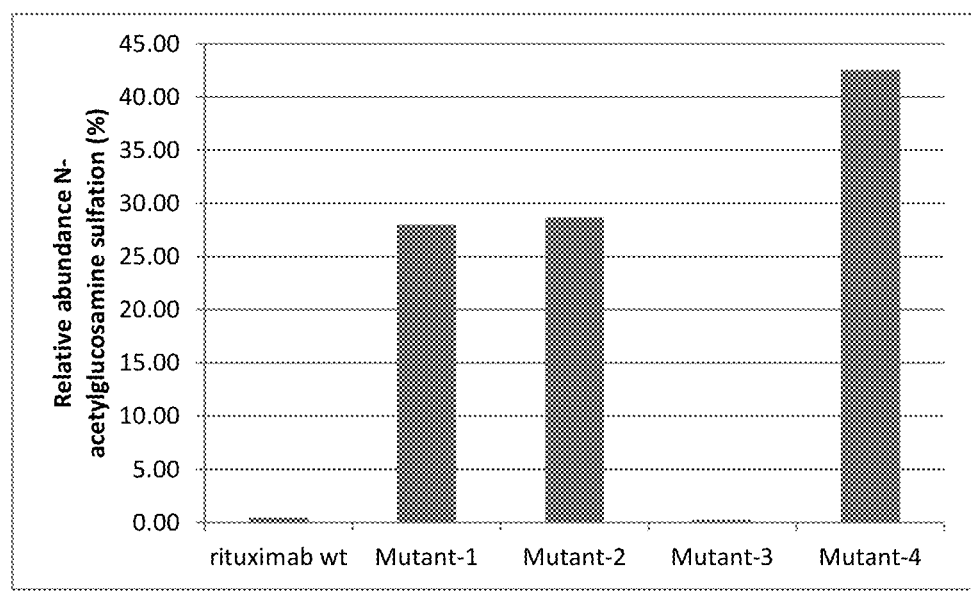
FIG. 5 is a diagrammatic representation of total sulfation of wild type (under chemical denaturation conditions) and mutant rituximab IgG1 antibodies.

Example 4—Characterization of Antibody Mutations on "Post Production" Glycosylation Certain modifications of N-glycans in the Fc domain of an IgG 1 molecule can be confounded by protein conformation. For example, the ability to sulfate an antibody can be affected by protein conformation. Disrupting the conformation of purified (post-production) wild type rituximab with increasing concentrations of a chemical denaturant (urea), followed by in vitro treatment with a sulfo-transferase, resulted in increasing levels of total sulfation of the antibody glycans. Introducing mutations into the Fc region also resulted in increased levels of sulfation in the presence of a sulfo-transferase in vitro. As shown in FIG. 5, mutants 1, 2, and 4 (but not mutant 3) exhibited increased levels of sulfation (in the absence of urea) compared to that of wild type rituximab (not treated with urea).

Figure 6:
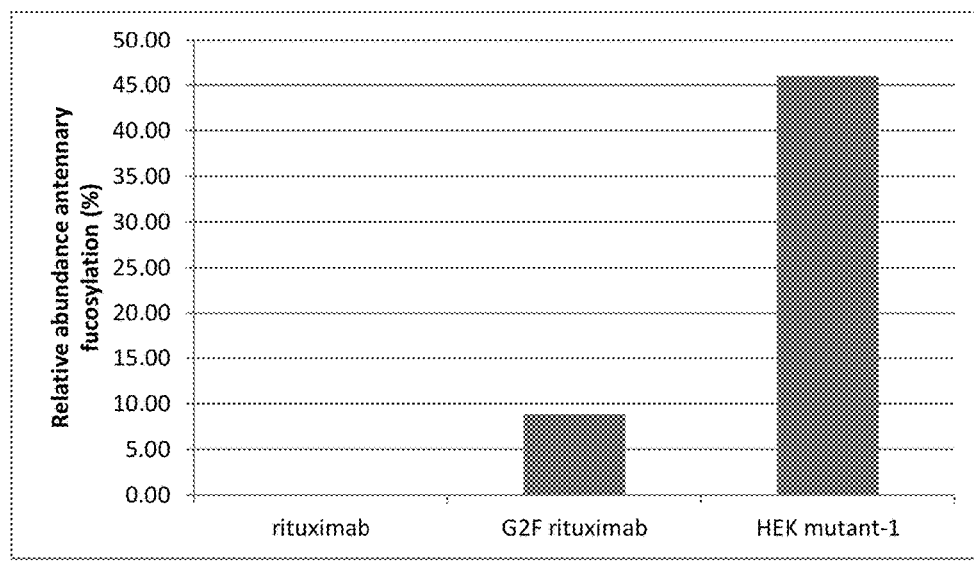
FIG. 6 is a diagrammatic representation of post-production fucosylation of wild type and mutant 1 of rituximab IgG1 antibody.

Similar results were observed when purified antibodies were incubated with a fucosyltransferase in vitro. As shown in FIG. 6, treatment of purified mutant 1 (predominantly G2F) with a fucosyltransferase resulted in a much greater level of fucosylation relative to wild type rituximab (IgG 1) or to G2F IgG 1 (predominantly G2F).

EQUIVALENTS

It is to be understood that while the disclosure has been described in conjunction with the detailed description thereof, the foregoing description is intended to illustrate and not limit the scope of the invention, which is defined by the scope of the appended claims. Other aspects, advantages, and modifications are within the scope of the following claims.

The invention claimed is:

1. A method of producing a preparation of recombinant glycoprotein, the method comprising:
expressing in a cell a recombinant glycoprotein comprising a modified amino acid sequence of a reference glycoprotein, the reference glycoprotein comprising an immunoglobulin Fc region or Fc fragment,
wherein the recombinant glycoprotein comprises an Fc region or Fc fragment comprising two amino acid substitutions relative to the Fc region or Fc fragment of the reference glycoprotein, wherein the two amino acid substitutions are F241A/F243A, F241A/K246A, F241A/T260A, F241A/R301A, F243A/K246A, F243A/T260A, F243A/R301A, K246A/T260A, K246A/R301A, or T260A/R301A, as numbered according to the EU numbering index of Kabat; and
isolating the recombinant glycoprotein, thereby producing the preparation of recombinant glycoprotein, wherein the preparation has an increased level of one or more of sialylated glycans, fucosylated glycans, and N-acetylglucosamine glycans, relative to a preparation of the reference glycoprotein.

2. The method of claim 1, wherein the recombinant glycoprotein of the preparation has a different Fc receptor affinity, Fc receptor specificity, complement activation activity, signaling activity, targeting activity, effector function, half-life, clearance, anti-inflammatory activity, or transcytosis activity than the reference glycoprotein.

3. The method of claim 2, wherein the effector function is antibody dependent cellular cytotoxicity, complement dependent cytotoxicity, programmed cell death, or cellular phagocytosis.

4. The method of claim 2, wherein the recombinant glycoprotein of the preparation has a different Fc receptor affinity or Fc receptor specificity than the reference glycoprotein, wherein the Fc receptor is an FcγRT, FcγRIIA, FcγRIIB, FcγRIIIA, FcγRIIIB, FcγRIV, or FcRn receptor.

5. The method of claim 4, wherein the recombinant glycoprotein of the preparation binds to a macrophage, neutrophil, or eosinophil.

6. The method of claim 1, wherein the reference glycoprotein is an antibody.

7. The method of claim 6, wherein the antibody is abciximab, adalimumab, alemtuzumab, basiliximab, bevacizumab, cetuximab, certolizumab, daclizumab, eculizumab, efalizumab, gemtuzumab, ibritumomab, infliximab, muromonab, natalizumab, omalizumab, palivizumab, panitumumab, ranibizumab, rituximab, tositumomab, or trastuzumab.

8. The method of claim 1, wherein the preparation of the recombinant glycoprotein comprises an increased level of sialylated glycans relative to a preparation of the reference glycoprotein.

9. The method of claim 1, wherein the preparation of the recombinant glycoprotein comprises an increased level of fucosylated glycans relative to a preparation of the reference glycoprotein.

10. The method of claim 1, wherein the preparation of the recombinant glycoprotein comprises an increased level of N-acetylglucosamine glycans relative to a preparation of the reference glycoprotein.

11. The method of claim 8, wherein the level of sialylated glycans is increased by 10% to 500% relative to a preparation of the reference glycoprotein.

12. The method of claim 9, wherein the level of fucosylated glycans is increased by 10% to 500% relative to a preparation of the reference glycoprotein.

13. The method of claim 10, wherein the level of N-acetylglucosamine glycans is increased by 10% to 500% relative to a preparation of the reference glycoprotein.

14. The method of claim 1, wherein the recombinant glycoprotein of the preparation comprises two Fc regions, wherein one of the two Fc regions comprises two amino acid substitutions relative to the Fc region of the reference glycoprotein, wherein the two amino acid substitutions are selected from the group consisting of F241A/F243A, F241A/K246A, F241A/T260A, F241A/R301A, F243A/K246A, F243A/T260A, F243A/R301A, K246A/T260A, K246A/R301A, and T260A/R301A, as numbered according to the EU numbering index of Kabat.

15. The method of claim 1, wherein the glycoprotein of the preparation comprises two Fc regions, wherein the two Fc regions each comprises two amino acid substitutions relative to the Fc region of the reference glycoprotein, wherein the two amino acid substitutions are selected from the group consisting of F241A/F243A, F241A/K246A, F241A/T260A, F241A/R301A, F243A/K246A, F243A/T260A, F243A/R301A, K246A/T260A, K246A/R301A, and T260A/R301A, as numbered according to the EU numbering index of Kabat.

\* \* \* \* \*

UNITED STATES PATENT AND TRADEMARK OFFICE
CERTIFICATE OF CORRECTION

PATENT NO. : 10,377,832 B2
APPLICATION NO. : 15/497057
DATED : August 13, 2019
INVENTOR(S) : Nathaniel Washburn et al.

It is certified that error appears in the above-identified patent and that said Letters Patent is hereby corrected as shown below:

In the Claims

At Column 53, Claim number 4, Line number 48, please replace the term "FcγRT" with "FcγRI".

Signed and Sealed this
Third Day of December, 2019

Andrei Iancu
*Director of the United States Patent and Trademark Office*